(12) United States Patent
Bodine

(10) Patent No.: US 7,098,372 B1
(45) Date of Patent: Aug. 29, 2006

(54) PHARMACEUTICAL COMPOSITIONS AND METHODS OF USING SECRETED FRIZZLED RELATED PROTEIN

(75) Inventor: Peter V. N. Bodine, Havertown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/169,545

(22) PCT Filed: Sep. 13, 2000

(86) PCT No.: PCT/US00/25035

§ 371 (c)(1),
(2), (4) Date: May 31, 2002

(87) PCT Pub. No.: WO01/19855

PCT Pub. Date: Mar. 22, 2001

Related U.S. Application Data

(63) Continuation-in-part of application No. 09/394,832, filed on Sep. 13, 1999, now abandoned.

(51) Int. Cl.
*G01N 33/00* (2006.01)
*A01K 67/027* (2006.01)

(52) U.S. Cl. ............................................. 800/3; 800/18
(58) Field of Classification Search .................. 800/3, 800/8, 13, 18, 14
See application file for complete search history.

(56) References Cited

OTHER PUBLICATIONS

Houdebine LM "Production of pharmaceutical proteins from transgenic animals." Journal of Biotechnology 34:269-287, 1994.*
Mullins et al. "Transgenesis in nonmurine species." Hypertension 22:630-633, 1993.*
Kappel et al. "Regulating gene expression in transgenic animals." Current Opinion in Biotechnology 3:548-553, 1992.*
Sigmund CD "Viewponit: are studies in genetically altered mice out of control?" Arterioscler Thromb Vasc Biol 20:1425-1429, 2000.*
Cameron ER "Recent advances in transgenic technology" Molecular Biotechnology 7:253-265, 1997.*
Wall RJ "New gene transfer methods." Theriogenology 57:189-201, 2002.*

* cited by examiner

*Primary Examiner*—Anne-Marie Falk
(74) *Attorney, Agent, or Firm*—Darby & Darby

(57) ABSTRACT

Pharmaceutical compositions and methods of use in regulation of mammalian bone forming activities of SFRPs (secreted frizzled-related proteins) are disclosed. SFRPs are secreted receptors for Wnts that are important polypeptide growth factors that are known to regulate fundamental biological processes like tissue polarity, embryonic development and tumorigenesis. A SFRP was isolated in human osteoblast cells and identified as SFRP-1 (also known as SARP-2) and shown to be regulated by osteogenic agents in the HOB cells in a differentiation selective manner modulating the life of osteoblasts/preosteocytes.

7 Claims, 30 Drawing Sheets

Osteogenic RADE Confirmation: SFRP
poly (A)+ RNA Northern Blot
(Probed with Cloned RADE Fragment)
HOB-03-C5 Cells
(Proliferative)
FIG.3

FIG. 4

Osteogenic RADE Confirmation: SFRP
*poly (A)+ RNA Northen Blot*
(Probed with Cloned 1.1 kb cDNA)
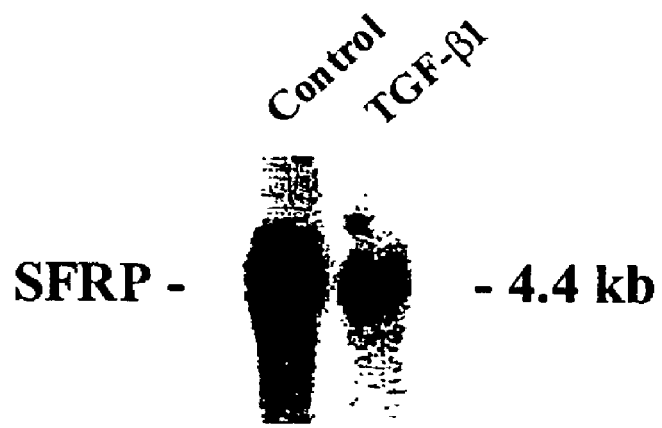
SFRP -        - 4.4 kb
SFRP/β-Actin:    1.0   0.2
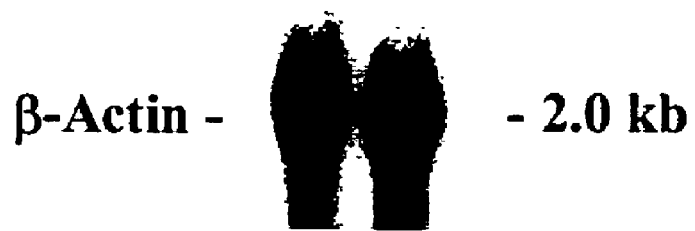
β-Actin -        - 2.0 kb
HOB-01-C1 Cells
(Pre-Osteocytic Stage)
FIG. 5

Osteogenic RADE Confirmation: SFRP
*poly(A)+ RNA Northern Blot*
(Probed with Cloned 1.1 kb Fragment)

Control
PTH
PGE2
TGF-β1
Control
PGE2

SFRP — −4.4 kb

SaOS-2    hOB

GAPDH — −1.4 kb

SFRP/GAPDH:   1.0  0.9  0.7  0.9   1.0  1.3

FIG. 7

FIG. 8 RT-PCR for the Coding Region of FRP-1/SARP-2 in HOB-03-CE6 Cells: Southern Blot with an Internal Oligonucleotide Probe AN INITIATION SITE-DIRECTED ANTISENSE OLIGONUCLEOTIDE FOR SARP-2
REVERSES THE INDUCTION OF CELL DEATH BY $PGE_2$ IN HOB-03-C5 CELLS AN INITIATION SITE-DIRECTED ANTISENSE OLIGONUCLEOTIDE FOR SARP-2
REVERSES THE INDUCTION OF CELL DEATH BY $PGE_2$ IN HOB-03-CE6 CELLS

SFRP-1 Mice: Age 16-18 Weeks
(Poly A+ RNA Northern Blot of Kidney)

Female Male
WT KO WT KO

SFRP-1                          4.4 kb

GAPDH                           1.4 kb

FIG. 20

SEQUENCE LISTING

<160> NUMBER OF SEQ ID NOS: 2

<210> SEQ ID NO 1
<211> LENGTH: 2602
<212> TYPE: DNA
<213> ORGANISM: Homo sapiens -continued

<400> SEQUENCE: 1

```
gatctgctgg ggactgcgcc ttttgtcccc ggaggtccct ggaagtttgc ggcgggacgc     60
gcgcggggag gcggcggagg cagccccgac gtcgcggaga acagggcgca gagccggcat    120
gggcatcggg cgcagcgagg ggggccgccg cggggcagcc ctgggcgtgc tgctggcgct    180
gggcgcggcg cttctggccg tgggctcggc cagcgagtac gactacgtga gcttccagtc    240
ggacatcggc ccgtaccaga gcgggcgctt ctacaccaag ccacctcagt gcgtggacat    300
ccccgcggac ctgcggctgt gccacaacgt gggctacaag aagatggtgc tgcccaacct    360
gctggagcac gagaccatgg cggaggtgaa gcagcaggcc agcagctggg tgcccctgct    420
caacaagaac tgccacgccg gcacccaggt cttcctctgc tcgctcttcg cgcccgtctg    480
cctggaccgg cccatctacc cgtgtcgctg gctctgcgag gccgtgcgcg actcgtgcga    540
gccggtcatg cagttcttcg gcttctactg gcccgagatg cttaagtgtg acaagttccc    600
cgagggggac gtctgcatcg ccatgacgcc gcccaatgcc accgaagcct ccaagcccca    660
aggcacaacg gtgtgtcctc cctgtgacaa cgagttgaaa tctgaggcca tcattgaaca    720
tctctgtgcc agcgagtttg cactgaggat gaaaataaaa gaagtgaaaa agaaaatgg    780
cgacaagaag attgtcccca agaagaagaa gccctgaag ttggggccca tcaagaagaa    840
ggacctgaag aagcttgtgc tgtacctgaa gaatggggct gactgtccct gccaccagct    900
ggacaacctc agccaccact tcctcatcat gggccgcaag gtgaagagcc agtacttgct    960
gacggccatc cacaagtggg acaagaaaaa caaggagttc aaaaacttca tgaagaaaat   1020
gaaaaaccat gagtgcccca cctttcagtc cgtgtttaag tgattctccc ggggcaggg    1080
aattctgcag atatccagca tggggaggga gcctcgggtg gggtgggagc gggggggaca   1140
gtgccccggg aacccggtgg gtcacacaca cgcactgcgc ctgtcagtag tggacattgt   1200
aatccagtcg gcttgttctt gcagcattcc cgctcccttc cctccatagc cacgctccaa   1260
accccagggt agccgtggcc gggtaaagca agggccattt agattaggaa ggttttttaag   1320
atccgcaatg tggagcagca gccactgcac aggaggaggt gacaaaccat ttccaacagc   1380
aacacagcca ctaaaacaca aaaggggga ttgggcggaa agtgagagcc agcagcaaaa   1440
actacattt gcaacttgtt ggtgtggatc tattggctga tctatgcctt tcaactagaa   1500
aattctaatg attggcaagt cacgttgttt tcaggtccag agtagtttct ttctgtctgc   1560
tttaaatgga aacagactca taccacactt acaattaagg tcaagcccag aaagtgataa   1620
gtgcagggag gaaaagtgca agtccattat gtagtagtga cagcaaaggg accaggggag   1680
aggcattgcc ttctctgccc acagtctttc cgtgtgattg tctttgaatc tgaatcagcc   1740
agtctcagat gccccaaagt ttcggttcct atgagcccgg ggcatgatct gatccccaag   1800
acatgtggag gggcagcctg tgcctgcctt tgtgtcagaa aaggaaacc acagtgagcc   1860
tgagagagac ggcgattttc gggctgagaa ggcggtagtt ttcaaaacac atagttaaaa   1920
aagaaacaaa tgaaaaaaat tttagaacag tccagcaaat tgctagtcag ggtgaattgt   1980
gaaattgggt gaagagctta cgattctaat ctcatgtttt ttccttttca cattttaaa    2040
agaacaatga caaacaccca cttatttttc aaggttttaa aacagtctac attgagcatt   2100
tgaaaggtgt gctagaacaa ggtctcctga tccgtccgag gctgcttccc agaggagcag   2160
ctctccccag gcatttgcca agggaggcgg atttccctgg tagtgtagct gtgtggcttt   2220
ccttcctgaa gagtccgtgg ttgccctaaa acctaacacc ccctagcaaa actcacagag   2280
cttttccgttt ttttctttcc tgtaaagaaa catttccttt gaacttgatt gcctatggat   2340
```

```
caaagaaatt cagaacagcc tgcctgtccc cccgcacttt ttacatatat ttgtttcatt    2400
tctgcagatg gaaagttgac atgggtgggg tgtccccatc cagcgagaga gtttcaaaag    2460
caaaacatct ctgcagtttt tcccaagtgc cctgagatac ttcccaaagc ccttatgttt    2520
aatcagcgat gtatataagc cagttcactt agacaacttt acccttcttg tccaatgtac    2580
aggaagtagt tctaaaaaaa aa                                              2602
```

<210> SEQ ID NO 2
<211> LENGTH: 314
<212> TYPE: PRT
<213> ORGANISM: Homo sapiens

<400> SEQUENCE: 2

```
Met Gly Ile Gly Arg Ser Glu Gly Gly Arg Gly Ala Ala Leu Gly
 1               5                  10                  15

Val Leu Leu Ala Leu Gly Ala Ala Leu Leu Ala Val Gly Ser Ala Ser
                20                  25                  30

Glu Tyr Asp Tyr Val Ser Phe Gln Ser Asp Ile Gly Pro Tyr Gln Ser
            35                  40                  45

Gly Arg Phe Tyr Thr Lys Pro Pro Gln Cys Val Asp Ile Pro Ala Asp
        50                  55                  60

Leu Arg Leu Cys His Asn Val Gly Tyr Lys Lys Met Val Leu Pro Asn
    65                  70                  75                  80

Leu Leu Glu His Glu Thr Met Ala Glu Val Lys Gln Gln Ala Ser Ser
                85                  90                  95

Trp Val Pro Leu Leu Asn Lys Asn Cys His Ala Gly Thr Gln Val Phe
            100                 105                 110

Leu Cys Ser Leu Phe Ala Pro Val Cys Leu Asp Arg Pro Ile Tyr Pro
        115                 120                 125

Cys Arg Trp Leu Cys Glu Ala Val Arg Asp Ser Cys Glu Pro Val Met
    130                 135                 140

Gln Phe Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Ala Thr Glu
                165                 170                 175

Ala Ser Lys Pro Gln Gly Thr Thr Val Cys Pro Pro Cys Asp Asn Glu
            180                 185                 190

Leu Lys Ser Glu Ala Ile Ile Glu His Leu Cys Ala Ser Glu Phe Ala
        195                 200                 205

Leu Arg Met Lys Ile Lys Glu Val Lys Lys Glu Asn Gly Asp Lys Lys
    210                 215                 220

Ile Val Pro Lys Lys Lys Pro Leu Lys Leu Gly Pro Ile Lys Lys
225                 230                 235                 240

Lys Asp Leu Lys Lys Leu Val Leu Tyr Leu Lys Asn Gly Ala Asp Cys
                245                 250                 255

Pro Cys His Gln Leu Asp Asn Leu Ser His His Phe Leu Ile Met Gly
            260                 265                 270

Arg Lys Val Lys Ser Gln Tyr Leu Leu Thr Ala Ile His Lys Trp Asp
        275                 280                 285

Lys Lys Asn Lys Glu Phe Lys Asn Phe Met Lys Met Lys Asn His
    290                 295                 300

Glu Cys Pro Thr Phe Gln Ser Val Phe Lys
305                 310
```

PHARMACEUTICAL COMPOSITIONS AND METHODS OF USING SECRETED FRIZZLED RELATED PROTEIN

This application is a 371 of PCT/US00/25035, filed Sep. 13, 2000, which is a continuation-in-part of application Ser. No. 09/394,832, filed Sep. 13, 1999, now abandoned.

FIELD OF THE INVENTION

The present invention relates to compositions and methods for regulating bone-forming activity. More particularly, the present invention relates to methods and pharmaceutical compositions for regulating bone forming activity with a secreted frizzled related protein (SFRP) derived form an osteoblast cell line, portions thereof, as well as antibodies and nucleic acids, including antisense, based thereon.

BACKGROUND OF THE INVENTION

The topic of bone formation regulation and bone-related disorders has recently gained considerable attention; for example in the women's health area, there has been a particular focus on the bone-related disorder of osteoporosis. Throughout life, there is a constant remodeling of skeletal bone. In this remodeling process, there is a fragile balance between bone formation by osteoblasts and subsequent bone resorption by osteoclasts.

As a normal part of the aging process the bone matrix undergoes various structural changes, the nature of which remains not fully determined. The majority of studies on age-related changes in human bone have been directed towards elucidating changes in bone on a morphological level or by quantitatively comparing rates of bone loss. Identification of the mechanisms involved in bone disorders is crucial for the understanding of bone physiology and bone disorders. While numerous genes and gene families and the polypeptides encoded by them that participate in the regulation of bone cells have been identified and cloned, their functions have not been clearly delineated due to the complexities of the bone formation pathways.

The WNT Gene Family

One group of genes and the proteins encoded by them that play an important role in regulating cellular development is the Wnt family of glycoproteins. Wnt proteins are a family of growth factors consisting of more than a dozen structurally related molecules and are involved in the regulation of fundamental biological processes like apoptosis, embryogenesis, organogenesis, morphogenesis and tumorigenesis (reviewed in Nusse and Varmus 1992 Cell 69: 1073–1087). These polypeptides are multipotent factors and have similar biological activities to other secretory proteins like transforming growth factor (TGF)-β, fibroblast growth factors (FGFs), nerve growth factor (NGF) and bone morphogenetic proteins (BMPs). One member of the Wnt growth factor family termed Wnt-x, is preferentially expressed in bone tissue and in bone-derived cells and appears to be involved in maintaining the mature osteoblast (bone-forming cell) phenotype (PCT/US94/14708; WO 95/17416).

The Frizzled Family of Proteins

Studies indicate that certain Wnt proteins interact with a family of proteins named "Frizzled" that act as receptors for Wnt proteins or as components of a Wnt receptor complex (reviewed in Moon et al. 1997 Cell 88: 725–728 and Barth et al. 1997 Curr. Opin. Cell Biol. 9: 683–690). Frizzled proteins contain an amino terminal signal sequence for secretion, a cysteine-rich domain (CRD) that is thought to bind Wnt, seven putative transmembrane domains that resemble a G-protein coupled receptor, and a cytoplasmic carboxyl terminus.

The discovery of the first secreted frizzled-related protein (SFRP) was reported by Hoang et al. in 1996 (J. Biol. Chem. 271: 26131–26137). This protein, which was called "Frzb" for frizzled motif in bone development, was purified and cloned from bovine articular cartilage extracts based on its ability to stimulate in vivo chondrogenic activity in rats. The human homologue of the bovine gene was also cloned. However, unlike the frizzled proteins, Frzb did not contain a serpentine transmembrane domain. Thus, this new member of the frizzled family appeared to be a secreted receptor for Wnt. The Frzb cDNA encoded for a 325 aa/36,000 Dalton protein and was predominantly expressed in the appendicular skeleton. The highest level of expression was in developing long bones and corresponded to epiphyseal chondroblasts; expression then declined and disappeared toward the ossification center.

Recent studies indicate SFRPs participate in apoptosis and thus some SFRPs have been identified as "SARPs" for secreted apoptosis related proteins. Additional members of the SFRP family have also recently been identified and shown to be antagonists of Wnt action. There are currently at least five known human SFRP/SARP genes: SFRP-1/FrzA/FRP-1/SARP-2, SFRP-2/SDF-5/SARP-1, SFRP-3/Frzb-1/FrzB/Fritz, SFRP-4 and SFRP-5/SARP-3 (Leimeister et al 1998 Mechanisms of Development 75: 29–42, which sequences of this reference are incorporated herein). Although the precise role that SARPs/SFRPs play in apoptosis is not yet clear, these proteins appear to either suppress or enhance the programmed cell death process.

In summary, a great need exists for the definitive identification of targets for the treatment of bone disorders, including bone resorption disorders such as osteoporosis and for regulation of bone formation in humans.

SUMMARY OF THE INVENTION

According to the present invention, there is provided methods and pharmaceutical compositions for regulating bone-forming activity in a mammal comprising a secreted frizzled related protein (SFRP) or regulating portion thereof. Additional compositions of the present invention employ antibodies formed from such proteins or portions thereof, and alternatively can employ nucleic acids that encode such proteins or portions thereof, including antisense sequences. In a preferred embodiment, the SFRP is from human osteoblast cells. The bone forming activities regulated by the composition of the present invention include the regulation of bone growth and bone density. The SFRP has the amino acid sequence set forth in SEQ ID NO: 2 which is obtained by the expression of the polynucleotide sequence set forth in SEQ ID NO 1. In the most preferred embodiment, the SFRP is SFRP-1 (SEQ ID NO 2).

In another aspect, methods of the present invention include methods for treating a bone disorder in a mammal, particularly a human comprising the steps of administering a pharmaceutical composition described above. As such, the methods for treating a bone disorder include but are not limited to disorders comprising the group consisting of (a) a bone formation disorder, (b) a bone resorption disorder and (c) a bone density disorder.

In another aspect of the invention, the bone disorder is a degenerative bone disorder wherein the degenerative bone disorder is selected from the group consisting of neurodegeneration, myodegeneration, and osteodegeneration disorders. The osteodegeneration disorder is selected from the group consisting of osteopenia, osteoarthritis, osteoporosis.

In an additional embodiment, the invention includes methods for identifying test compounds regulating SFRP activity. In the method, the compounds regulating the bone-forming activity in a mammal are assayed by first incubating a sample comprising a SFRP in a test medium containing the test compound. The next step is to determine the SFRP activity, wherein an increase in activity relative to SFRP alone indicates the compound is a SFRP activator and a decrease in activity indicates the compound is a SFRP inhibitor.

In a further embodiment, the invention includes methods of modulating Wnt-mediated signaling in a cell comprising contacting said cell with the SFRP described above, wherein said Wnt activity is regulated.

The present invention additionally relates to a method of facilitating bone formation or repair in a bone cell culture, comprising isolating the cells from a bone culture, introducing a recombinant construct expressing SFRP having the amino acid sequence set forth in SEQ ID NO: 2, and returning said cells into the bone culture. Preferably, the construct expresses an antisense sequence for a nucleic acid sequence which encodes all or a portion of a SFRP protein.

Another embodiment relates to a polynucleotide probe capable of hybridizing with the polynucleotide having the nucleic acid sequence set forth in SEQ ID NO: 1. Such probe is used in a diagnostic process for detecting a SFRP polynucleotide in a sample derived from a mammalian host comprising detecting the presence or absence of the SFRP in the sample.

BRIEF DESCRIPTION OF THE DRAWINGS

FIG. 3 shows an autoradiogram of a Northern blot of poly A+ RNA isolated from the hOB-03-C5 cells after treatment with control, PGE$_2$ and TGF-β1 for 24 hr. In this experiment, both the cloned hOB SFRP RADE gene fragment and a cloned GAPDH cDNA were used as probes. Once again, the hOB SFRP mRNA is completely up-regulated by treatment of the cells with PGE$_2$.

FIG. 4 shows an autoradiogram of a Northern blot of poly A+ RNA isolated from either the hOB-03-CE6 or hOB-01-C1 cells after treatment with control, PTH, PGE$_2$ and TGF-β1 for 24 hr. In this experiment, both the excised hOB SFRP RADE gene fragment and a cloned GAPDH cDNA were used as probes. The arrow points to the hOB SFRP mRNA that is completely up-regulated by treatment of the hOB-03-CE6 cells with PGE$_2$, but is down-regulated by treatment of the hOB-01-C1 cells with PTH. It can also be seen that the hOB-01-C1 cells express high basal levels of the mRNA.

FIG. 5 shows an autoradiogram of a Northern blot of poly A+ RNA isolated from the hOB-01-C1 cells after treatment with control and TGF-β1 for 24 hr. In this experiment, both the full-length (1.1 kb) cloned hOB SFRP cDNA and a cloned beta-Actin cDNA were used as probes. The results show that the hOB SFRP mRNA is down-regulated by treatment of the cells with TGF-β1. Once again, it can also be seen that the hOB-01-C1 cells express high basal levels of the mRNA.

FIG. 7 shows an autoradiogram of a Northern blot of poly A+ RNA isolated from SaOS-2 human osteosarcoma osteoblast-like cells and explant cultures of normal human osteoblasts (hOB) after treatment with control, PTH, PGE$_2$ and TGF-β1 for 24 hr. In this experiment, both the full-length cloned hOB SFRP cDNA and a cloned GAPDH cDNA were used as probes. The results show that the SaOS-2 cells express low basal levels of hOB SFRP mRNA which is not regulated by these agents. In contrast, hOB cells express moderate levels of this message which is up-regulated by treatment with PGE$_2$. TaqMan quantitative RT-PCR analysis of hOB cells treated with PGE$_2$ indicated that PGE$_2$ upregulated SFRP message levels 10-fold.

FIG. 20 depicts a Northern blot of poly A+ RNA isolated from female and male kidneys obtained from the wild-type (WT) and knock-out (KO) SFRP-1 mice. This blot shows that the WT kidneys express high levels of SFRP-1 mRNA (4.4 kb), while the KO kidneys do not express this gene.

DETAILED DESCRIPTION OF THE INVENTION

Figure 1:
FIG. 1 shows the osteogenic RADE results that lead to the discovery of the human osteoblast (hOB) secreted frizzled-related protein (SFRP) cDNA. The figure shows autoradiograms of differential-display polymerase chain reaction (DD-PCR) gels from the experiments performed with the three hOB cell lines (hOB-03-C5, hOB-03-CE6 and hOB-01-C1) in three different stages of differentiation (proliferative-stage, maturation-stage and pre-osteocytic). The arrow points to the 276 base pair (bp) hOB SFRP gene fragment (i.e., RADE fragment) that is up-regulated by PGE$_2$ treatment in the hOB-03-C5 and hOB-03-CE6 cells, but is down-regulated by TGF-β1 treatment in the hOB-01-C1 cells. It can also be seen that the hOB-01-C1 cells express high basal levels of this gene. A basic local alignment search tool (BLAST) search of this gene fragment against the public databases indicated that this cDNA was homologous to the mouse SFRP-1 and bovine FrzA genes.
Figure 2:
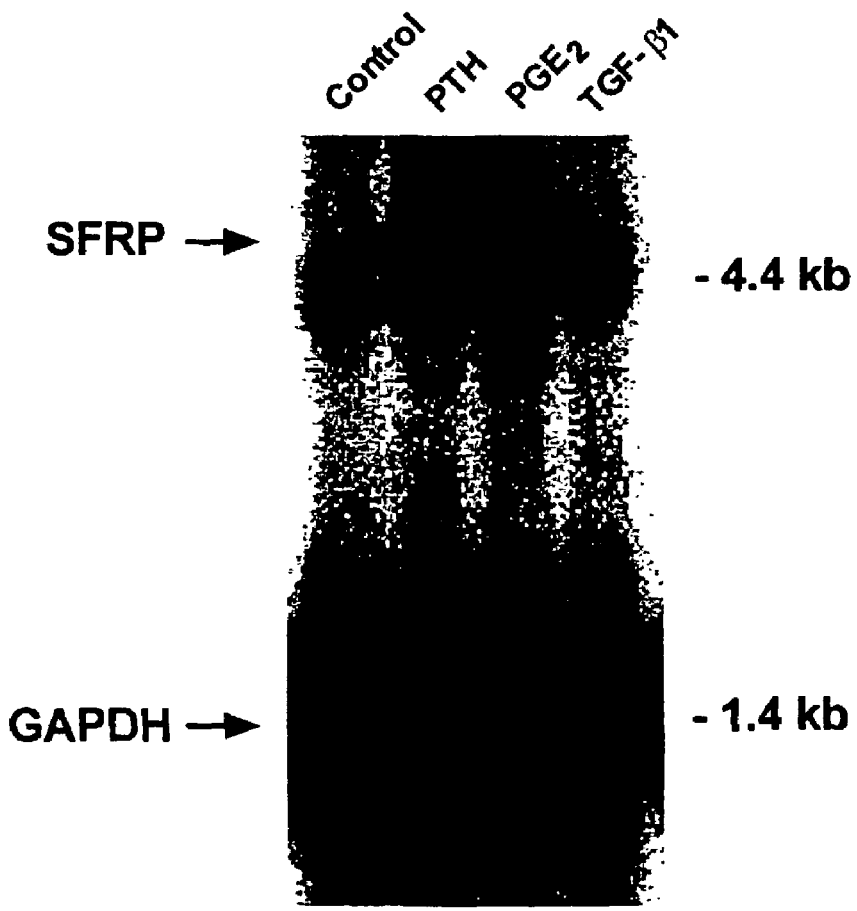
FIG. 2 shows an autoradiogram of a Northern blot of poly A+ RNA isolated from the hOB-03-C5 cells after treatment with control, PTH, PGE$_2$ and TGF-β1 for 24 hr. In this experiment, both the excised hOB SFRP RADE gene fragment and a cloned glyceraldehyde phosphate dehydrogenase (GAPDH) cDNA were used as probes. The arrow points to the hOB SFRP mRNA (~4.4 kb) which is completely up-regulated by treatment of the cells with PGE$_2$.

The present invention relates to a gene whose expression is regulated by osteogenic or bone-forming agents in three different human osteoblast (hOB) cell lines in vitro. In one aspect of the present invention, the expression of this gene is upregulated during hOB differentiation, suggesting it may be involved in the bone formation process. DNA sequence analysis indicated that this gene fragment shared significant sequence identity to a mouse cDNA called secreted frizzled-related protein (SFRP)-1 (Rattner et al. 1997 Proc. Natl. Acad. Sci. USA 94: 2859–2863). Subsequent cDNA cloning and additional sequence analysis indicated that this gene, which is referred to as the hOB SFRP, was identical to human FRP-1/SARP-2 (Finch et al. 1997 Proc. Natl. Acad. Sci. USA 94: 6770–6775; Melkonyan et al. 1997 Proc. Natl. Acad. Sci. USA 94: 13636–13641). Characterization of the hOB SFRP contemplates its use as a novel osteoporotic drug target and in a novel drug screen for identifying anabolic bone agents.

Definitions

The term "bone formation" is the process of bone synthesis and mineralization. The osteoblast cell modulates the process.

The term "bone growth" is the process of skeletal expansion. This process occurs by one of two ways: (1) intramembraneous bone formation arises directly from mesenchymal or bone marrow cells; (2) longitudinal or endichindual bone formation arises where bone from cartilage.

The term "osteogenesis" is synonymous with the term bone formation, defined above.

The terms "secreted frizzled related proteins" or "SFRP" is a secreted receptor of the Wnt signaling pathway and exhibits a number of characteristics that make it a useful tool for studying cell growth and differentiation. The frizzled like gene family encodes cell membrane proteins having transmembrane domains with unknown functions.

The terms "secreted apoptosis related protein" or "SARP" are synonymous with the term secreted frizzled related proteins or SFRPs defined above.

The terms "proteins", "peptides" and "polypeptides" are used interchangeably and are intended to include purified and recombinantly produced SFRP molecules containing amino acids linearly coupled through peptide bonds. The amino acids of this invention can be in the L or D form so long as the biological activity of the polypeptide is maintained. The SFRP proteins of this invention may also include proteins that are post-translationally modified by reactions that include glycosylation, acetylation and phosphorylation. Such polypeptides also include analogs, alleles and allelic variants that can contain amino acid derivatives or non-amino acid moieties that do not affect the biological or functional activity of the SFRP protein as compared to wild-type or naturally occurring protein. The term amino acid refers both to the naturally occurring amino acids and their derivatives, such as TyrMe and PheCl, as well as other moieties characterized by the presence of both an available carboxyl group and an amine group. Non-amino acid moieties that can be contained in such polypeptides include, for example, amino acid mimicking structures. Mimicking structures are those structures that exhibit substantially the same spatial arrangement of functional groups as amino acids but do not necessarily have both the amino and carboxyl groups characteristic of amino acids.

"Muteins" are SFRP proteins or polypeptides that have minor changes in amino acid sequence caused, for example, by site-specific mutagenesis or other manipulations; by errors in transcription or translation; or which are prepared synthetically by rational design. These minor alterations result in amino acid sequences wherein the biological activity of the protein or polypeptide is altered as compared to wild-type or naturally occurring polypeptide or protein. Examples of muteins include the SFRP-1 of SEQ. ID. No. 2 described herein.

As used herein, the term "hydrophobic" is intended to include those amino acids, amino acid derivatives, amino acid mimics and chemical moieties that are non-polar. Hydrophobic amino acids include Phe, Val, Trp, Ile, and Leu. As used herein, the term "positively charged amino acid" refers to those amino acids, amino acid derivatives, amino acid mimics and chemical moieties that are positively charged. Positively charged amino acids include, for example, Lys, Arg and His.

"Purified" when referring to a SFRP protein or polypeptide, is distinguishable from native or naturally occurring proteins or polypeptides because they exist in a purified state. These "purified" SFRP proteins or polypeptides, or any of the intended variations as described herein, shall mean that the compound or molecule is substantially free of contaminants normally associated with the compound in its native or natural environment. The terms "substantially pure" and "isolated" are not intended to exclude mixtures of polynucleotides or polypeptides with substances that are not associated with the polynucleotides or polypeptides in nature.

"Native" SFRP polypeptides, proteins, or nucleic acid molecules refer to those SFRP recovered from a source occurring in nature or "wild-type".

A "composition" is intended to mean a combination of active agent, i.e., the SFRP of the present invention and another compound or composition, inert (for example, a detectable agent or label) or active, such as an adjuvant.

A "pharmaceutical composition" is intended to include the combination of SFRP, particularly SFRP-1 as the active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, Remington's Pharm. Sci., 15th Ed. (Mack Publ. Co. Easton (1975)).

The term "nucleic acid" as it relates to the SFRP described herein means single and double stranded DNA, cDNA, genome-derived DNA, and RNA, as well as the positive and negative strand of the nucleic acid that are complements of each other, including anti-sense RNA. A "nucleic acid molecule" is a term used interchangeably with "polynucleotide" and each refers to a polymeric form of nucleotides of any length, either ribonucleotides or deoxyribonucleotides, or analogs thereof. It also includes known types of modifications, for example labels which are known in the art (e.g., Sambrook et al. (1989) infra.), methylation, "caps", substitution of one or more of the naturally occurring nucleotides with an analog, internucleotide modifications such as, for example, those with uncharged linkages (e.g., methyl carbamate, etc.), those containing pendant moieties, such as for example, proteins (including, e.g., nuclease, toxins, antibodies, signal peptides, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. The polynucleotide can be chemically or biochemically modified or contain non-natural or derivatized nucleotide bases. The nucleotides may be complementary to the mRNA encoding the polypeptides. These complementary nucleotides include, but are not limited to, nucleotides capable of forming triple helices and antisense nucleotides. Recombinant polynucleotides comprising sequences otherwise not naturally occurring are also provided by this invention, as are alterations of wild-type polypeptide sequences, including but not limited to, those due to deletion, insertion, substitution of one or more nucleotides or by fusion to other polynucleotide sequences.

A SFRP polynucleotide is said to "encode" a SFRP polypeptide if, in its native state or when manipulated by methods well-known to those skilled in the art, it can be transcribed and/or translated to produce a polypeptide or mature protein. Thus, the term polynucleotide shall include, in addition to coding sequences, processing sequences and other sequences that do not code for amino acids of the mature protein. The anti-sense strand of such a polynucleotide is also said to encode the sequence.

The term "recombinant" polynucleotide or DNA refers to a polynucleotide that is made by the combination of two otherwise separated segments of sequence accomplished by the artificial manipulation of isolated segments of DNA by genetic engineering techniques or by chemical synthesis. In so doing, one may join together DNA segments of desired functions to generate a desired combination of functions.

An "analog" of a SFRP DNA, RNA or a polynucleotide, refers to a macromolecule resembling naturally occurring polynucleotides in form and/or function (particularly in the ability to engage in sequence-specific hydrogen bonding to base pairs on a complementary polynucleotide sequence) but which differs from DNA or RNA in, for example, the possession of an unusual or non-natural base or an altered backbone. See for example, Uhlmann et al. (1990) *Chemical Reviews* 90:543–584.

"Isolated when referring to a SFRP nucleic acid molecule, means separated from other cellular components normally associated with native or wild-type SFRP DNA or RNA intracellularly.

"Hybridization" refers to hybridization reactions that can be performed under conditions of different "stringency". Conditions that increase the stringency of a hybridization reaction are widely known and published in the art: see, for example, Sambrook et al., infra. Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%, incubation times from 5 minutes to 24 hours and washes of increasing duration, increasing frequency, or decreasing buffer concentrations.

"$T_m$" is the temperature in degrees Centigrade at which 50% of a polynucleotide duplex made of complementary strands hydrogen bonded in an antiparallel direction by Watson-Crick base paring dissociates into single strands under the conditions of the experiment. $T_m$ may be predicted according to standard formula, for example:

$$T_m = 81.5 + 16.6 \log [Na^+] + 0.41(\% \ G/C) - 0.61(\%F) - 600/L$$

where Na+ is the cation concentration (usually sodium ion) in mol/L; (% G/C) is the number of G and C residues as a percentage of total residues in the duplex; (% F) is the percent formamide in solution (wt/vol); and L is the number of nucleotides in each strand of the duplex.

A "stable duplex" of polynucleotides, or a "stable complex" formed between any two or more components in a biochemical reaction, refers to a duplex or complex that is sufficiently long lasting to persist between the formation of the duplex or complex, and its subsequent detection. The duplex or complex must be able to withstand whatever conditions exist or are introduced between the moment of formation and the moment of detection, these conditions being a function of the assay or reaction which is being performed. Intervening conditions which may optionally be present and which may dislodge a duplex or complex include washing, heating, adding additional solutes or solvents to the reaction mixture (such as denaturants), and competing with additional reacting species. Stable duplexes or complexes may be irreversible or reversible, but must meet the other requirements of this definition. Thus, a transient complex may form in a reaction mixture, but it does not constitute a stable complex if it dissociates spontaneously or as a result of a newly imposed condition or manipulation introduced before detection.

When stable duplexes form in an antiparallel configuration between two single-stranded polynucleotides, particularly under conditions of high stringency, the strands are essentially "complementary". A double-stranded polynucleotide can be "complementary" to another polynucleotide, if a stable duplex can form between one of the strands of the first polynucleotide and the second. A complementary sequence predicted from the sequence of single stranded polynucleotide is the optimum sequence of standard nucleotides expected to form hydrogen bonding with the single-stranded polynucleotide according to generally accepted base-pairing rules.

A "sense" strand and an "antisense" strand when used in the same context refer to single-stranded SFRP polynucleotides which are complementary to each other. They may be opposing strands of a double-stranded polynucleotide, or one strand may be predicted from the other according to generally accepted base-pairing rules. Unless otherwise specified or implied, the assignment of one or the other strand as "sense" or "antisense" is arbitrary.

A linear sequence of SFRP nucleotides is "identical" to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotide, the sequence for the DNA reflects the order of nitrogenous bases in the polydeoxyribonucleotide, and the two sequences satisfy the other requirements of this definition. Where at least one of the sequences is a degenerate oligonucleotide comprising an ambiguous residue, the two sequences are identical if at least one of the alternative forms of the degenerate oligonucleotide is identical to the sequence with which it is being compared. For example, AYAAA (SEQ ID NO 3) is identical to ATAAA (SEQ ID NO 4), if AYAAA (SEQ ID NO 5) is a mixture of ATAAA (SEQ ID NO6) and ACAAA (SEQ ID NO 7).

When comparison is made between polynucleotides, it is implicitly understood that complementary strands are easily generated, and the sense or antisense strand is selected or predicted that maximizes the degree of identity between the polynucleotides being compared. For example, where one or both of the polynucleotides being compared is double-stranded, the sequences are identical if one strand of the first polynucleotide is identical with one strand of the second polynucleotide. Similarly, when a polynucleotide probe is described as identical to its target, it is understood that it is the complementary strand of the target that participates in the hybridization reaction between the probe and the target.

A linear sequence of nucleotides is "essentially identical" or the "equivalent" to another linear sequence, if both sequences are capable of hybridizing to form duplexes with the same complementary polynucleotide. It should be understood, although not always explicitly stated that Applicants refer to a specific nucleic acid molecule, its equivalents are also intended. Sequences that hybridize under conditions of greater stringency are more preferred. It is understood that hybridization reactions can accommodate insertions, deletions, and substitutions in the nucleotide sequence. Thus, linear sequences of nucleotides can be essentially identical even if some of the nucleotide residues do not precisely correspond or align. Sequences that correspond or align more closely to the invention disclosed herein are comparably more preferred. Generally, a polynucleotide region of about 25 residues is essentially identical to another region, if the sequences are at least about 80% identical; more preferably, they are at least about 90% identical; more preferably, they are at least about 95% identical; still more preferably, the sequences are 100% identical. A polynucleotide region of 40 residues or more will be essentially identical to another region, after alignment of homologous portions if the sequences are at least about 75% identical; more preferably, they are at least about 80% identical; more preferably, they are at least about 85% identical; even more preferably, they are at least about 90% identical; still more preferably, the sequences are 100% identical.

In determining whether polynucleotide sequences are essentially identical, a sequence that preserves the functionality of the polynucleotide with which it is being compared is particularly preferred. Functionality can be determined by different parameters. For example, if the polynucleotide is to be used in reactions that involve hybridizing with another polynucleotide, then preferred sequences are those which hybridize tot he same target under similar conditions. In general, the $T_m$ of a DNA duplex decreases by about 10° C. for every 1% decrease in sequence identity for duplexes of 200 or more residues; or by about 50° C. for duplexes of less than 40 residues, depending on the position of the mismatched residues (see, e.g. Meinkoth et al.). Essentially identical or equivalent sequences of about 100 residues will generally form a stable duplex with each other's respective complementary sequence at about 20° C. less than $T_m$; preferably, they will form a stable duplex at about 15° C. less; more preferably, they will form a stable duplex at about 10° C. less; even more preferably, they will form a stable duplex at about 5° C. less; still more preferably, they will form a stable duplex at about $T_m$. In another example, if the polypeptide encoded by the polynucleotide is an important part of its functionality, then preferred sequences are those which encode identical or essentially identical polypeptides. Thus, nucleotide differences which cause a conservative amino acid substitution are preferred over those which can cause a non-conservative amino acid substitution are preferred over those which cause a non-conservative substitution, nucleotide differences which do not alter the amino acid sequence are more preferred, while identical nucleotides are even more preferred. Insertions or deletions in the polynucleotide that result in insertions or deletions in the polypeptide are preferred over those that result in the down-stream coding regions being rendered out of phase; polynucleotide sequences comprising no insertions or deletions are even more preferred. The relative importance of hybridization properties and the encoded polypeptide sequence of a polynucleotide depends on the application of the invention.

A polynucleotide has the same characteristics or is the equivalent of another polynucleotide if both are capable of forming a stable duplex with a particular third polynucleotide under similar conditions of maximal stringency. Preferably, in addition to similar hybridization properties, the polynucleotides also encode essentially identical polypeptides.

"Conserved" residues of a polynucleotide sequence are those residues that occur unaltered in the same position of two or more related sequences being compared. Residues that are relatively conserved are those that are conserved amongst more related sequences than residues appearing elsewhere in the sequences.

"Related" polynucleotides that share a significant proportion of identical residues.

As used herein, a "degenerate" oligonucleotide sequence is a designed sequence derived from at least two related originating polynucleotide sequences as follows: the residues that are conserved in the originating sequences are preserved in the degenerate sequence, while residues that are not conserved in the originating sequences may be provided as several alternatives in the degenerate sequence. For example, the degenerate sequence AYASA (SEQ ID NO 8) may be assigned from originating sequences ATACA (SEQ ID NO 9) and ACAGA (SEQ ID NO 10), where Y is C or T and S is C or G. Y and S are examples of "ambiguous" residues. A degenerate segment is a segment of a polynucleotide containing a degenerate sequence.

It is understood that a synthetic oligonucleotide comprising a degenerate sequence is actually a mixture of closely related oligonucleotides sharing an identical sequence, except at the ambiguous positions. Such an oligonucleotide is usually synthesized as a mixture of all possible combinations of nucleotides at the ambiguous positions. Each of the oligonucleotides in the mixture is referred to as an "alternative form".

A polynucleotide "fragment" or "insert" as used herein generally represents a sub-region of the full-length form, but the entire full-length polynucleotide may also be included.

Different polynucleotides "correspond" to each other if one is ultimately derived from another. For example, messenger RNA corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides also "correspond" to each other if they serve a similar function, such as encoding a related polypeptide, in different species, strains or variants that are being compared.

A "probe" when used in the context of SFRP polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is an oligonucleotide, generally with a free 3'-OH group, that binds to a target potentially present in a sample of interest by hybridizing with the target, and thereafter promotes polymerization of a polynucleotide complementary to the target.

Processes of producing replicate copies of the same polynucleotide, such as PCR or gene cloning, are collectively referred to herein as "amplification" or "replication". For example, single or double-stranded DNA may be replicated to form another DNA with the same sequence. RNA may be replicated, for example, by and RNA-directed RNA polymerase, or by reverse-transcribing the DNA and then performing a PCR. In the latter case, the amplified copy of the RNA is a DNA with the identical sequence.

A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme. Generally, a PCR involves reiteratively forming three steps: "annealing", in which the temperature is adjusted such that oligonucleotide primers are permitted to form a duplex with the polynucleotide to be amplified; "elongating", in which the temperature is adjusted such that oligonucleotides that have formed a duplex are elongated with a DNA polymerase, using the polynucleotide to which they have formed the duplex as a template; and "melting", in which the temperature is adjusted such that the polynucleotide and elongated oligonucleotides dissociate. The cycle is then repeated until the desired amount of amplified polynucleotide is obtained. Methods for PCR are taught in U.S. Pat. No. 4,683,195 to Mullis and U.S. Pat. No. 4,683,202 to Mullis et al.

Elements within a gene include but are not limited to promoter regions, enhancer regions, repressor binding regions, transcription initiation sites, ribosome binding sites, translation initiation sites, protein encoding regions, introns and exons, and termination sites for transcription and translation. An "antisense" copy of a particular polynucleotide refers to a complementary sequence that is capable of hydrogen bonding to the polynucleotide and can therefor, be capable of modulating expression of the polynucleotide. These are DNA, RNA or analogs thereof, including analogs having altered backbones, as described above. The polynucleotide to which the antisense copy binds may be in single-stranded form or in double-stranded form.

As used herein, the term "operatively linked" means that the DNA molecule is positioned relative to the necessary regulation sequences, e.g., a promoter or enhancer, such that the promoter will direct transcription of RNA off the DNA molecule in a stable or transient manner.

"Vector" means a self-replicating nucleic acid molecule that transfers an inserted nucleic acid molecule into and/or between host cells. The term is intended to include vectors that function primarily for the replication of nucleic acid and expression vectors that function for transcription and/or translation of the DNA or RNA. Also intended are vectors that provide more than one of the above functions.

"Host cell" is intended to include any individual cell or cell culture that can be or have been recipients for vectors or the incorporation of exogenous nucleic acid molecules and/or proteins. It also is intended to include progeny of a single cell, and the progeny may not necessarily be completely identical (in morphology or in genomic or total DNA complement) to the original parent cell due to natural, accidental, or deliberate mutation.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody (as defined above) and its binding partner or ligand.

A "suitable cell" for the purposes of this invention is one that includes but is not limited to a cell expressing the SFRP, e.g., a bone marrow cell, preferentially an hOB cell.

A "biological equivalent" of a nucleic acid molecule is defined herein as one possessing essential identity with the reference nucleic acid molecule. A fragment of the reference nucleic acid molecule is one example of a biological equivalent.

A "biological equivalent" of an SFRP polypeptide or protein is one that retains the same characteristic as the reference protein or polypeptide. It also includes fragments of the reference protein or polypeptide.

The SFRP proteins and polypeptides also can be obtained by chemical synthesis using a commercially available automated peptide synthesizer such as those manufactured by Applied Biosystems, Inc., Model 430A or 431A, Foster City, Calif. and the amino acid sequence provided in SEQ. ID NO 2. The synthesized protein or polypeptide can be precipitated and further purified, for example by high performance liquid chromatography (HPLC). Accordingly, this invention also provides a process for chemically synthesizing the proteins of this invention by providing the sequence of the protein (e.g., SEQ. ID NO 2) and reagents, such as amino acids and enzymes and linking together the amino acids in the proper orientation and linear sequence.

Alternatively, the proteins and polypeptides can be obtained by well-known recombinant methods as described, for example, in Sambrook et al. *Molecular Cloning: A Laboratory Manual* 2d ed. (Cold Spring Harbor Laboratory (1989)) using, for example, the host cell and vector systems described and exemplified below. This invention further provides a process for producing a SFRP, analog, mutein or fragment thereof, by growing a host cell containing a nucleic acid molecule encoding the desired protein, the nucleic acid being operatively linked to a promoter of RNA transcription. The desired protein may be introduced into the host cell by use of a gene construct which contains a promoter and termination sequence for the nucleic acid sequence of the desired protein. The host cell is grown under suitable conditions such that the nucleic acid is transcribed and translated into protein. In a separate embodiment, the protein is further purified.

The proteins of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant that is useful to nonspecifically augment a specific immune response. A skilled artisan can easily determine whether an adjuvant is required and selects one. However, for the purpose of illustration only, suitable adjuvants include, but are not limited to Freund's Complete and Incomplete, mineral salts and polynucleotides.

Therapeutic Applications for SFRPs/SARPs

Although the SFRPs/SARPs gene family has only recently been discovered and there is still much to learn about its biology, there are nevertheless several potential therapeutic applications for these proteins. Since Wnts have been implicated as proto-oncogenes, SFRPs/SARPs may serve as tumor suppressors due to their ability to antagonize Wnt activity. These proteins may also be utilized in tissue regeneration. For example, since FrzB-1 stimulated ectopic chondrogenic activity in vivo, it could be used to accelerate fracture repair or the healing of joints after hip and knee replacement (patent application number WO 98/16641 A1). Finally, since SFRPs/SARPs appear to control apoptosis, these proteins could also be utilized to treat a variety of degenerative diseases including neurodegeneration, myodegeneration and osteodegeneration disorders.

Pharmaceutical Compositions

This invention also provides compositions containing any of the above-mentioned proteins, muteins, fragments, antibodies, nucleic acid molecules encoding such proteins, muteins, antibodies or fragments thereof, as well as vectors and host cells that express such nucleic acid molecules, and an acceptable solid or liquid, carrier buffer, or diluent. An effective amount of one or more active ingredient is used which sufficient to accomplish the desired regulatory effect on a bone-forming activity or apoptosis activity. An effective amount can be determined by conventional dose-response curves for the desired activity. When the compositions are used pharmaceutically, they are combined with a "pharmaceutically acceptable carrier" for diagnostic and therapeutic use. The formulation of such compositions is well known to persons skilled in this field. Pharmaceutical compositions of the invention may comprise one or more additional active components and, preferably, include a pharmaceutically acceptable carrier. The additional active component may be provided to work in combination with an active based on a one or more SFRPs, as described above. In alternative embodiments, the additional active is added since it works on the same disease or disorder as SFRPs but by a different mode of action from those actives based on SFRPs, or the additional active may work on other diseases or disorders present in a human or animal. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The term "pharmaceutically acceptable carrier" refers to a carrier that does not cause an allergic reaction or other untoward effect in patients to whom it is administered. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of one or more of the active components of the composition. The use of such media and agents for pharmaceutically active substances is well known in the art. Except insofar as any conventional media or agent is incompatible with the active ingredient, use thereof in immunogenic compositions of the present invention is contemplated.

These compositions also can be used for the preparation of medicaments for the diagnosis and treatment of pathologies associated neurodegenerative (i.e., Huntington's disease, Alzheimer's disease, spinal cord injuries), myodegerative (i.e., muscular dsytrophy, myasthenia gravis, myotonic myopathies) and osteodegenerative disorders (i.e., osteoporosis).

In certain embodiments, antibodies that binds all or a portion of an SFRP protein are employed in the composition to treat of any of the above diseases or disorders. Polyclonal and monclonal antibodies can be prepared by conventional methods. Generally, an antibody is raised against an amino acid sequence (a) that is specific to a SFRP protein (or proteins) and (b) that is also more likely to be antigenic. One can select a sequence specific for an SFRP protein by performing sequence analysis and using any conventional programs for sequence alignment and sequence comparisons. An amino acid sequence that is hydrophilic at one or more ends, preferably at both ends, is generally preferred for raising antibodies. In addition to employing amino acids that are hydrophilic, in preferred embodiments the hydrophilic amino acids are also basic (non-acidic). One can also employ any amino acid that increases antigenicity. For example, often prolines are employed in the center portion of the sequence. Antigenicity can be measured by an increase in decrease in the amount of antibody that is produced when generating antibodies against an initial test sequence, which is specific an SFRP protein(s). In certain embodiments of the present invention, the antibody is raised against a sequence comprising at least 8 consecutive amino acids of an SFRP protein(s), and preferably a sequence comprising at least 10 consecutive amino acids of an SFRP protein(s). In further preferred embodiments, the antibody is raised against amino acid sequence comprising about 15 to about 30 amino acids. In preferred embodiments, the antibody is raised against a sequence comprising at amino acids 217–231 of an SFRP protein of SEQ ID NO 2 or sequence variations thereof.

The compositions of the present invention can be administered to an individual in need of facilitated neural, muscle cartilage and bone growth by numerous routes, including but not limited to intravenous, subcutaneous, intramuscular, intrathecal, intracranial and topical. The composition may be administered directly to an organ or to organ cells by in vivo or ex vivo methods.

These compositions may be in soluble or microparticular form, or may be incorporated into microspheres or microvesicles, including micelles and liposomes.

INDUSTRIAL APPLICABILITY

The compositions described above provide the components for an assay to screen for agents and pharmaceutical compounds that are agonists or antagonists of a Wnt receptor in a suitable cell.

It is also anticipated that the SFRP polynucleotides of the invention will have utility as diagnostic agents or detecting genetic abnormalities associated with genes encoding SFRP or with one or more genes involved in the Wnt signaling pathway. Such genetic abnormalities include point mutations, deletions, or insertions of nucleotides. Any of several genetic screening procedures may be adapted for use with probes enabled by the present invention, including restriction fragment length polymorphism (RFLP) analysis, ligase chain reaction, or PCR. Mutations in this gene indicate increased risk of developmental abnormalities.

As provided in more detail below, the proteins and fragments thereof are useful in a cell-free and cellular in vitro assay system to screen for agents and pharmaceutical compounds which either inhibit or augment the Wnt-receptor pathway and apoptosis and to test possible therapies for disorders associated with this pathway, e.g., bone formation diseases, carcinogenesis, and cardiovascular diseases. Embryogenesis also can be modulated.

Drug screening assays can be used to identify activators or inhibitors of the SFRP protein. For example, an increase in cartilage growth in the presence of a drug compared to SFRP alone may indicate activation of SFRP, while a decrease may indicate inhibition of the SFRP activity.

A variety of compounds may be screened using methods of the present invention. They include peptides, macromolecules, small molecules, chemicals and biological mixtures. Such compounds may be biological, synthetic, organic, or inorganic compounds.

In the present invention suitable cells are used for preparing diagnostic assays, for the expression of SFPRs or for preparing nucleotide-based diagnostic kits. The cells may be made or derived from yeast, bacteria fungi, or viruses. In preferred embodiments, the cells are hOB cells, in particular a novel immortalized pre-osteocytic cell line referred to as hOB-01-C1-PS-09 cells (which are deposited with American Type Culture Collection in Manassas, Va. with the designation PTA-785), and osteoblast cells having the identifying characteristics of hOB-01-C1-PS-09 cells as well as osteoblast cells made therefrom, e.g. progeny. Immortalized refers to a substantially continuous and permanently established cell culture with substantially unlimited cell division potential. That is, the cells can be cultured substantially indefinitely, i.e., for at least about 6 months under rapid conditions of growth, preferably much longer under slower growth conditions, and can be propagated rapidly and continually using routine cell culture techniques. Alternatively stated, the cells of the present invention can be cultured for at least about 100, 150 or 200 population doublings. These cells produce a complement of proteins characteristic of normal human osteoblastic cells and are capable of osteoblastic differentiation. They can be used in cell culture studies of osteoblastic cell sensitivity to various agents, such as hormones, cytokines, and growth factors, or in tissue therapy. These cells are a post-senescent subclone of hOB-01-C1 cell line, as previously disclosed by Bodine et al 1996 Endocrinology 137:4592–4604.

Since, as we report herein, SFRPs are new drug targets for osteoporosis, certain embodiments relate to the expression of genes or nucleic acids that encode all or portion of at least one SFRP protein. Expression of such nucleic acids or genes in human osteoblast (hOB) cell lines correlates with accelerated cell death and apoptosis. The hOB-01C1PS-09 cells of this invention are particularly useful over other hOB cells since the present "-09" cells are adult osteoblast cells. In addition, these cells are osteocytic (i.e. mature cells) in comparison to other hOB cells which are often osteoblastic. Furthermore, the hOB-01-C1-PS-09 cells express very low levels of FRP-1/SARP-2 message. Consequently, the hOB-01-C1-PS-09 cell line will be a unique in vitro model to study the effects of FRP-1/SARP-2 reintroduction and over-expression. Another important feature of the hOB-01-C1-PS-09 cells is that they can be used for both transient and stable transfection studies. Some of the many advantages of this cell over the parental hOB-01-C1 cells are as follows: the hOB-01-C1-PS-09 cells are truly immortal, they divide 2- to 3-times faster at 34° C., and yet they retain many of the pre-osteocytic characteristics of the parental cells.

The hOB-01-C1-PS-09 cells will be useful for establishing stable cell lines that over-express potential osteoporotic drug targets. Such stable cell lines will then be valuable for characterizing these drug targets, as well as for developing high throughput screens and assays to identify compounds that regulate them.

EXAMPLES

The present invention is further described by the following examples. The examples are provided solely to illustrate the invention by reference to specific embodiments. These exemplifications, while illustrating certain specific aspects of the invention do not portray the limitations or circumscribe the scope of the invention.

Example A

Generation and Analysis of hOB Cells

The hOB-01-C1 cells are a conditionally-transformed cell line derived from adult human bone that faithfully exhibit a pre-osteocytic phenotype. These cells were transformed with a temperature-sensitive large T-antigen (tsA 209) and proliferate at the permissive temperature of 34° C. when the T-antigen mutant is active; however, the cells stop dividing at the non-permissive temperature ($\geq$37° C.) when the T-antigen mutant is inactive. Although the hOB-01-C1 cells are the first osteocyte cell line to be established and are suitable for exploratory research, they have some disadvantages for drug discovery. Like other SV-40 large T-antigen transformed human cell lines, the hOB-01-C1 cells undergo crisis and senesce after 15–20 passages in culture. Thus, although often referred to as "immortal", such cell lines are actually only "extended-life". The hOB-01-C1 cells also proliferate slowly in culture at 34° C. with a doubling time of about once every 5 to 6 days. In order to overcome some of these draw-backs, the hOB-01-C1-PS-09 cell line was established.

The hOB-01-C1-PS-09 cells were developed by passaging the parental hOB-01-C1 cell line beyond the crisis point (i.e., passages 15–20) until proliferation resumed (passages 20–25). The post-senescent cells were then expanded in culture and sub-cloned. Clones were characterized using reverse transcriptase-polymerase chain reaction (RT-PCR) analysis to measure the levels of expression of parathyroid hormone (PTH)-1 receptor mRNA. The hOB-01-C1-PS-09 cells were chosen for further characterization, since this clone expressed the highest level of PTH-1 receptor message at 39° C. This cell line went through approximately 20–25 population doublings during the cloning and expansion procedure, and has subsequently been passaged over 50-times. These cell line can be passaged hundreds of times. Thus, the hOB-01-C1-PS-09 cells are truly an immortal cell line.

Like the parental hOB-01-C1 cell line, the hOB-01-C1-PS-09 cells fail to form monolayer cultures and leave spaces on the tissue culture dishes.

The cells also appear to form cell-to-cell contacts through long cellular processes. From analysis by electron microscopy, the cells possess finger-like cellular projections that are reminiscent of pre-osteocytes, and these processes form gap junctions when they contact adjacent cells. As with the parental cell line, the hOB-01-C1-PS-09 cells also express the tsA 209 large T-antigen as determined by immunocytochemistry.

Figure 22A:
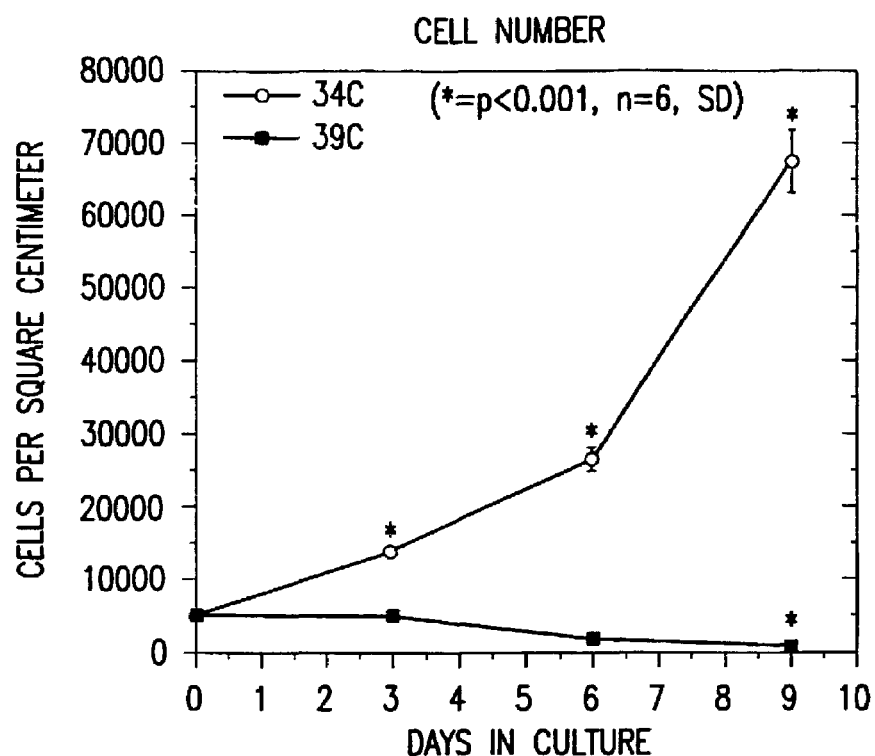
FIG. 22 is a set of graphs showing (A) cell proliferation of hOB cells (B) the ability/enhancement in hOB cells for vitamin $D_3$-treatment to up-regulate alkaline phosphatase activity at 39° C., and (C) the inability of vitamin $D_3$ to induce osteocalcin secretion from hOB cells at 34° C., as detailed in Example A.
Figure 22B:
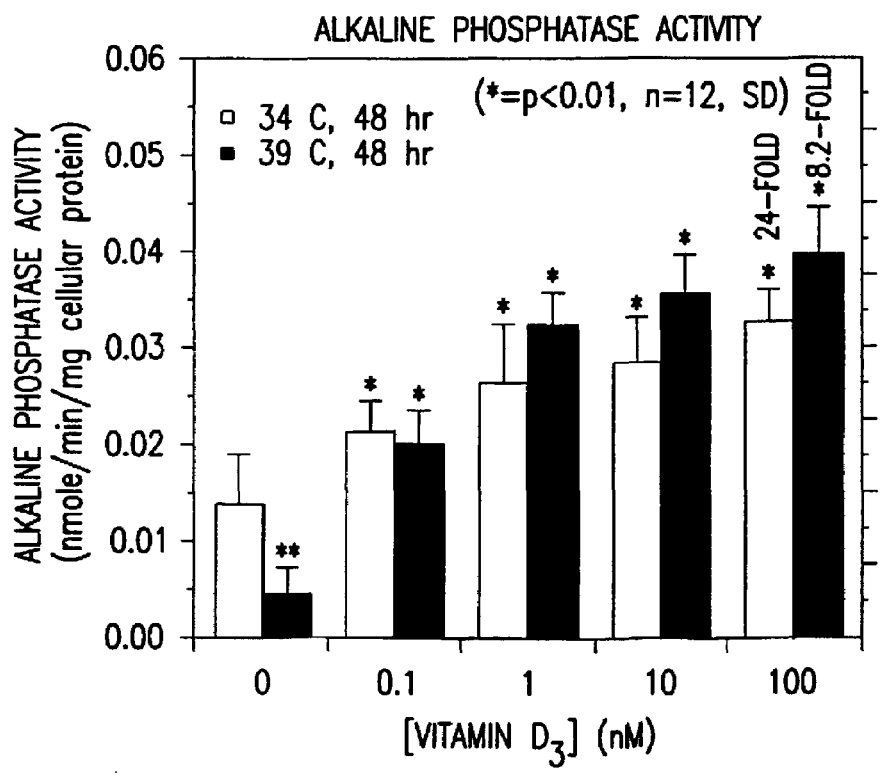
Figure 22C:
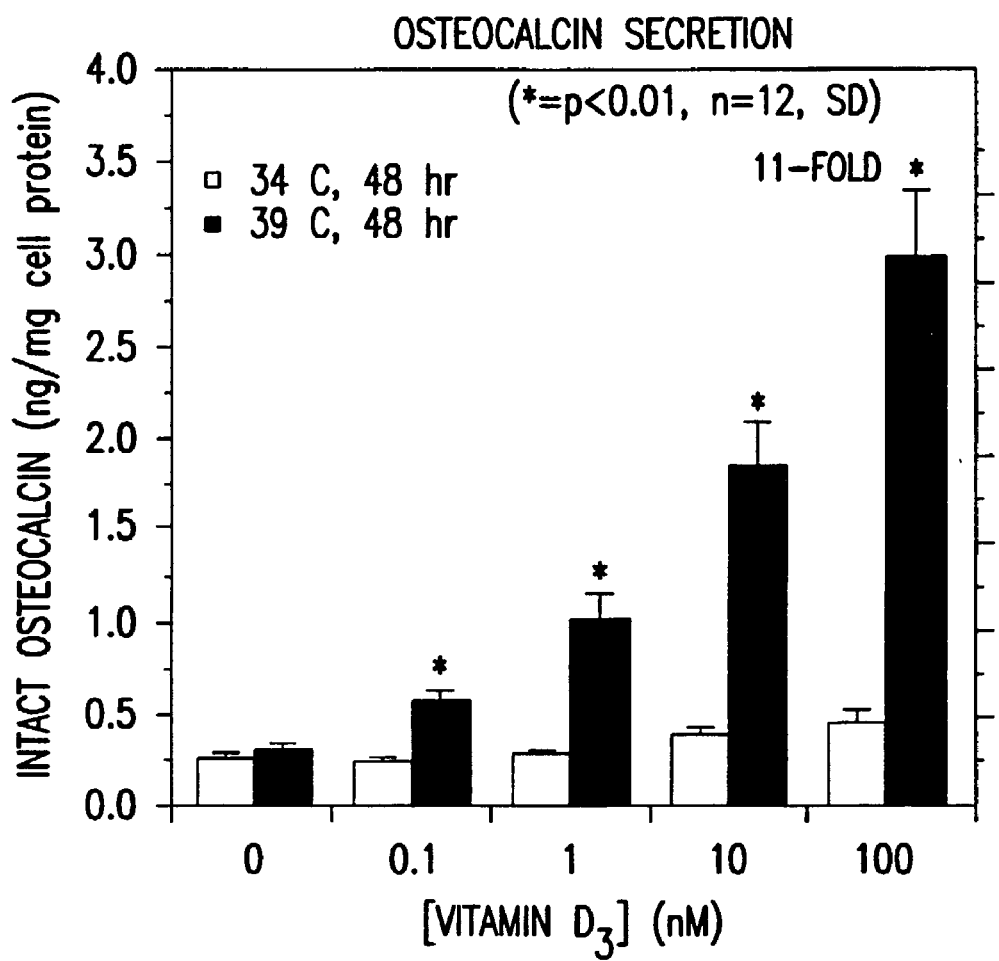

Unlike the parental hOB-01-C1 cell line, the hOB-01-C1-PS-09 cells proliferate 2- to 3-times faster at the permissive temperature with a doubling time of once every 2–3 days (FIG. 22A). However, like the parental cells, the hOB-01-C1-PS-09 cells stop dividing at the non-permissive temperature (FIG. 22A). This observation indicates that although the cells have passed through the crisis point and become immortal, they still require an active T-antigen for proliferation. Moreover, as with the parental cell line, the hOB-01-C1-PS-09 cells require inactivation of the T-antigen in order to exhibit an enhanced osteocytic phenotype. Alkaline phosphatase and osteocalcin are two important markers of the osteocytic lineage. As shown in FIG. 22B, the ability of vitamin $D_3$-treatment to up-regulate alkaline phosphatase activity is enhanced about 4-fold when the cells are incubated at 39° C. Furthermore, as depicted in FIG. 22C, vitamin $D_3$ is unable to induce osteocalcin secretion from the cells at 34° C.

However, the secosteroid up-regulates production of this bone-specific matrix protein 11-fold when the cells are incubated at 39° C. It should be noted that the basal levels of alkaline phosphatase expression and osteocalcin secretion by the hOB-01-C1-PS-09 cells are similar to the parental cell line. Thus, both morphologically and biochemically, the hOB-01-C1-PS-09 cells resemble the parental hOB-01-C1 cells and are therefore a reliable in vitro model to study human pre-osteocyte biology.

Figure 23:
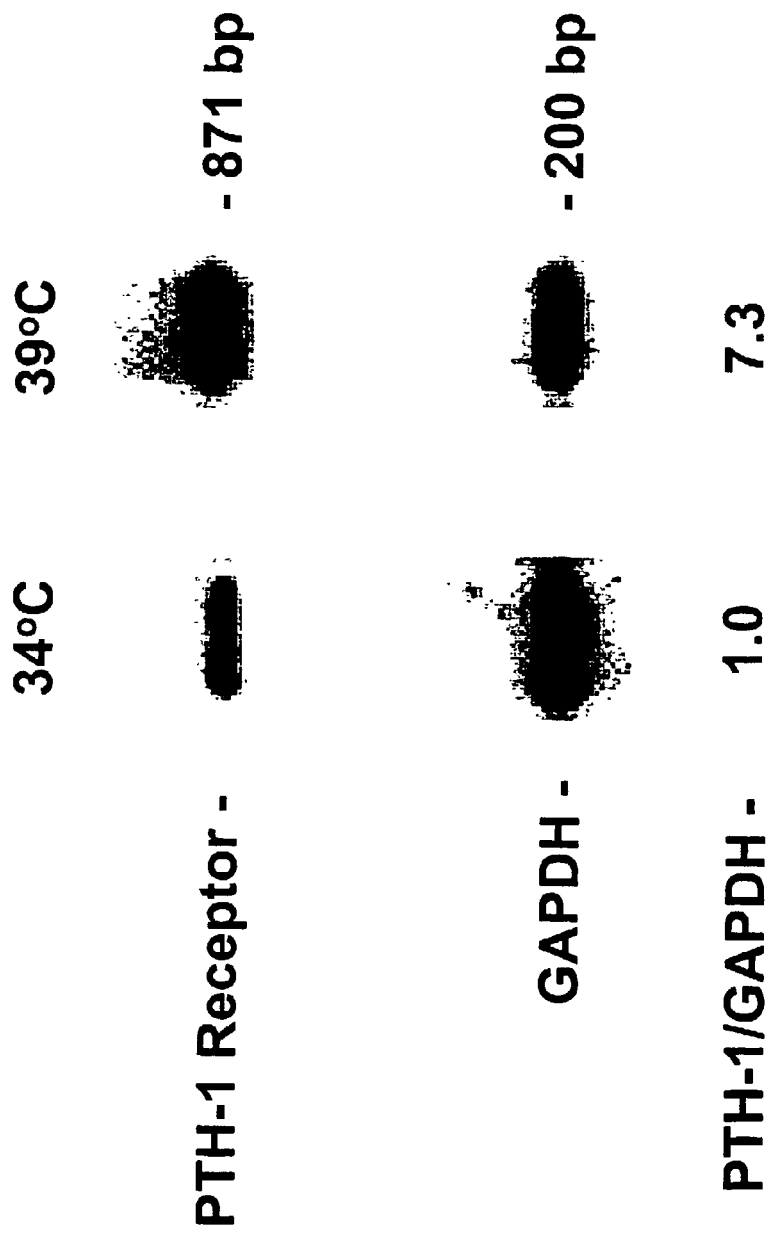
FIG. 23 depicts the results from Example A regarding the expression of PTH-1 receptor mRNA expression; wherein incubation of the hOB cells ells for 48 hours at 39° C. increases the steady-state message levels for PTH-1 receptor by 7-fold when compared to cells maintained at 34° C.
Figure 24:
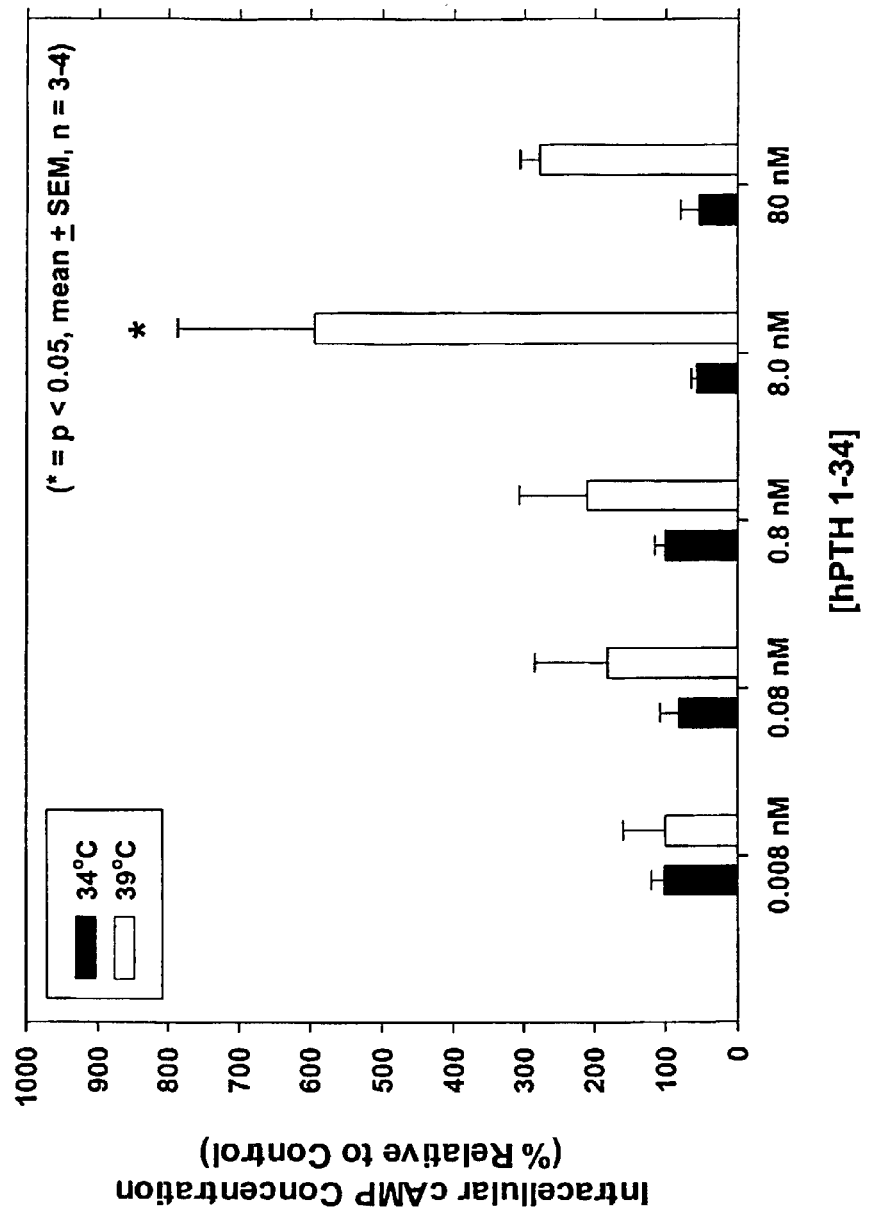
FIG. 24 depicts the results from Example A for the effect on intracellular cyclic adenosine monophosphate (cAMP) in response to increasing concentrations of PTH 1–34 in the hOB cells.

As mentioned above, the hOB-01-C1-PS-09 cell line was selected for further characterization based on its high-level of PTH-1 receptor mRNA expression. As shown in FIG. 23, incubation of the cells for 48 hr at 39° C. increases the steady-state message levels for the PTH-1 receptor by 7-fold when compared to cells maintained at 34° C. Since PTH-1 receptor expression is a marker of osteoblast/osteocyte differentiation, this is another indication that the cells exhibit a more pronounced osteocytic phenotype at the non-permissive temperature. Consistent with this enhanced PTH-1 receptor expression, preincubation of the hOB-01-C1-PS-09 cells for 48 hr at 39° C. followed by treatment with increasing concentrations of human PTH 1–34 (hPTH 1–34) for 10 min at 37° C. generates a dose-dependent 5- to 6-fold increase in intracellular cyclic-adenosine monophosphate (cAMP) levels (FIG. 24). In contrast, preincubation of the cells at 34° C. does not result in a subsequent increase in cAMP concentrations after hPTH 1–34 treatment. Thus, both PTH-1 receptor expression and responsiveness are enhanced following inactivation of the tsA-209 T-antigen. One potential utility for this cAMP assay would be the ability to characterize the activities of PTH-analogs or -mimetics in an important target cell under conditions where levels of PTH-1 receptor expression are dramatically altered.

Figure 25:
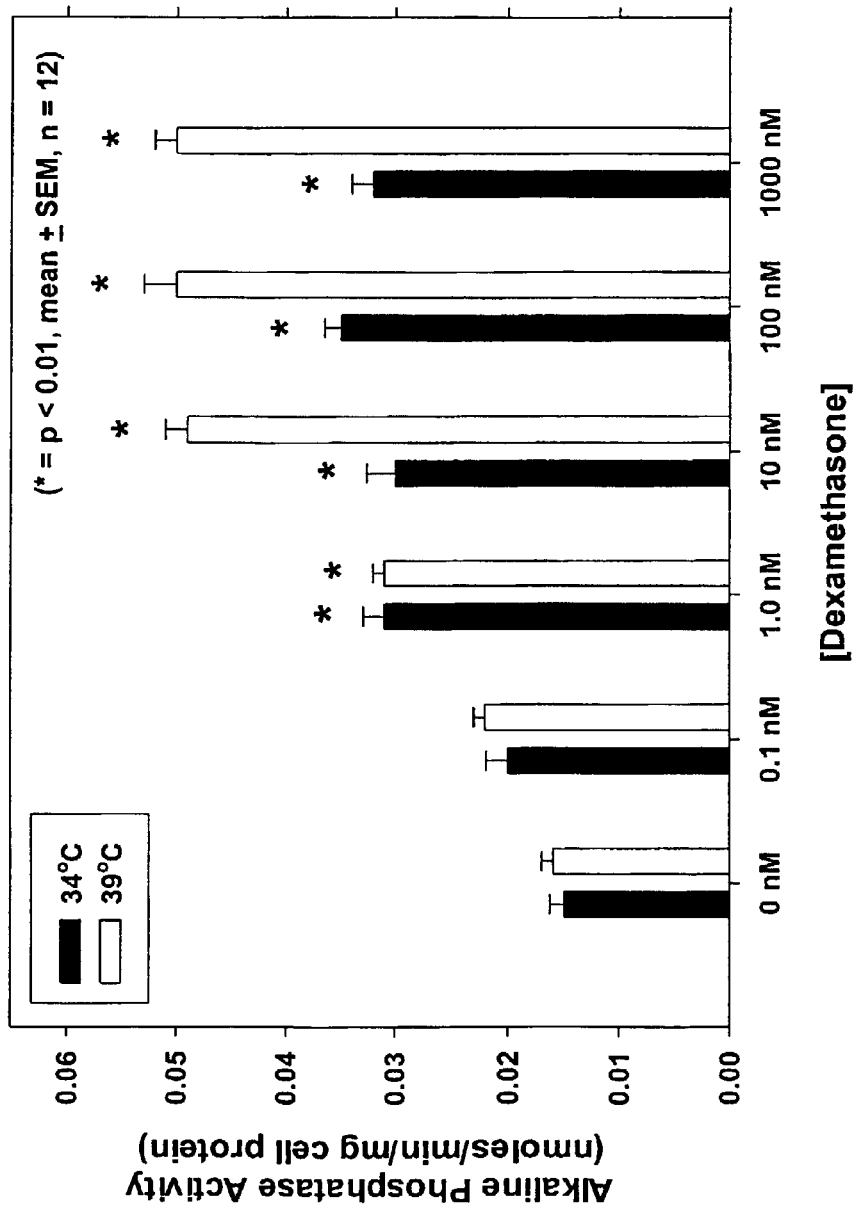
FIG. 25 is a graph which depicts the effect of hOB cells when treated with synthetic glucorticoid dexamethasone, which up-regulates alkaline phosphatase activity, as detailed in Example A.

In addition to vitamin $D_3$ and PTH, the hOB-01-C1-PS-09 cells also respond to additional bone-active agents: for example, glucocorticoids and transforming growth factor (TGF)-β1. Treatment of the cells with the synthetic glucocorticoid, dexamethasone, up-regulates alkaline phosphatase activity approximately 2-fold at 34° C. (FIG. 25), and this effect is once again enhanced when the cells are incubated at 39° C. Likewise, treatment of the cells with recombinant human (rh) TGF-β1 at 39° C. results in a dose-dependent decrease in hepatocyte growth factor (HGF) secretion. HGF has been shown to act as a chemotactic factor for osteoclasts, and may therefore play a role in regulating bone resorption.

Figure 26:
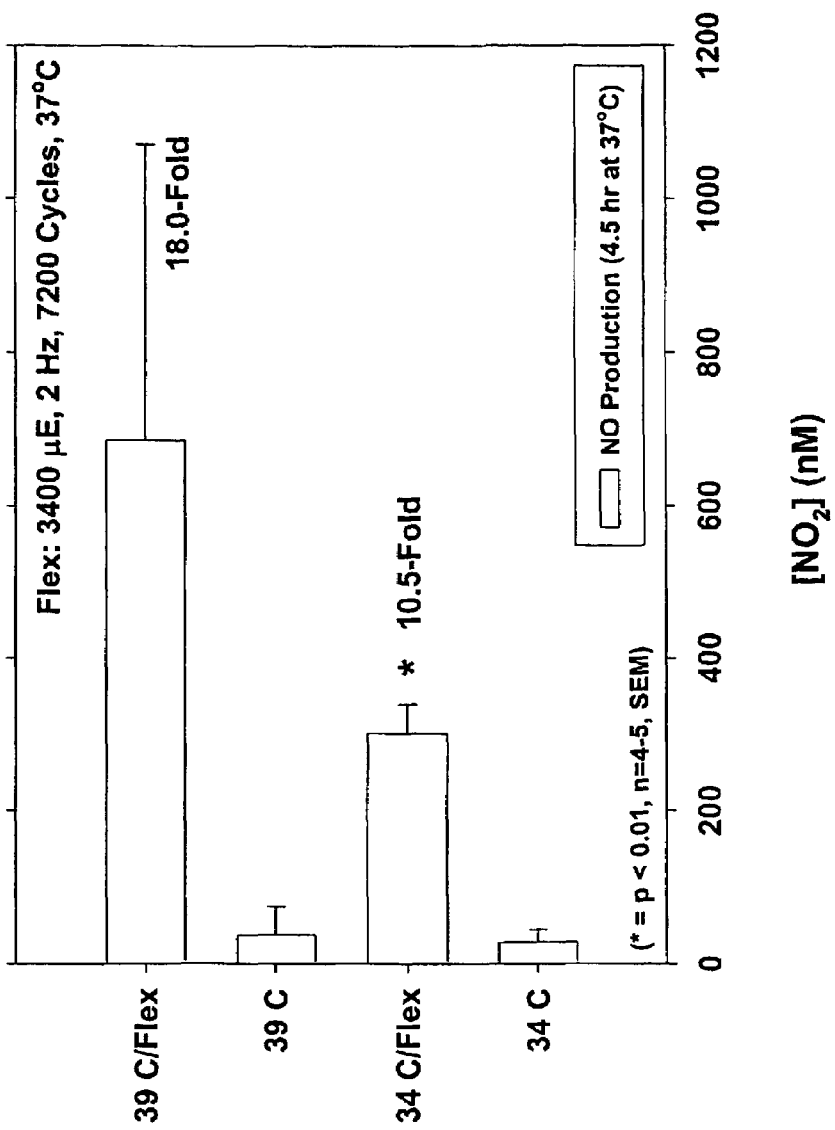
FIG. 26 depicts the results from experiments on the effect of mechanosensory stimulation on pre-osteocytic hOB cells, when subject to a Flexerall Strain Unit.

An important property of osteocytes is the ability to respond to mechanosensory stimulation, such as that which occurs during weight-bearing exercise. One method to simulate this stimulatory effect in vitro is through the use of a Flexercell Strain Unit (Flexcell International, Hillsborough, N.C.). For this experiment depicted in FIG. 26, the hOB-01-C1-PS-09 cells were seeded onto BioFlex type I collagen coated 6-well tissue culture dishes and incubated at 34° C. for 24 hr. The cells were then pre-incubated in serum-free medium at either 34° C. or 39° C. for an additional 24 hr, and then subjected to a physiologically-relevant strain (3400 µE, 2 Hz, 7200 cycles) at 37° C. using an FX-3000 Flexercell Strain Unit. After the strain-treatment, the cells were incubated for 4.5 hr, at which time the conditioned medium was collected and analyzed for the presence of nitric oxide (NO). It has been previously reported that in vitro mechanosensory stimulation or shear-stress of rodent and chick osteoblasts and osteocytes stimulates NO production. As shown in FIG. 26, mechanosensory stimulation (i.e., "Flex") of the hOB-01-C1-PS-09 cells enhances the production of NO by 10- to 18-fold. Consequently, these data suggest that this cell line will be a useful in vitro model to study the molecular mechanisms of mechanosensory stimulation.

Additional experiments establish that the hOB-01-C1-PS-09 cells can be used for both transient and stable transfection studies. This cell line can be transfected using the Tfx-20 lipofection reagent (Promega, Madison, Wis.). In such an experiment, the cells are seeded into 24-well tissue culture dishes at varying densities and then transfected with 0.25 µg/well of β-galactosidase and luciferase expression plasmids (total DNA=0.5 µg/well). After a 48 hr incubation at either 34° C. or 39° C., cell lysates are assayed for β-galactosidase and luciferase activity. From such experiments, results establish that the levels of either β-galactosidase or luciferase expression increase with increasing cell number. Moreover, when the luciferase expression is normalized to β-galactosidase expression in order to control for transfection efficiency, the level of luciferase expression is 2- to 3-fold higher when the cells are incubated at 34° C. Since luciferase expression is under the control of the SV-40 promoter, this observation is consistent with the tsA 209 T-antigen being inactivated at 39° C. Consequently, since these cells are both immortal and capable of being transfected, they can be used to develop stable over-expressing cell lines in a human pre-osteocytic background.

Example 1

Isolation of SFRP

The hOB SFRP gene fragment was identified using RADE (rapid analysis of differential expression) technology as described by Shiue 1997 Drug Develop. Res. 41: 142–159, the whole of which is incorporated herein. Three hOB cell lines (hOB-03-C5, hOB-03-CE6 and hOB-01-C1), representing three distinct stages of differentiation (proliferative, mature and preosteocytic, respectively) were used to isolate and identify SFRP. The hOB cell lines were established and cultured as previously described (Bodine et al. 1996 *J. Bone Miner. Res.* 11: 806–819; Bodine et al. 1996 *Endocrinology* 137: 4592–4604; Bodine et al. 1997 *J. Cell. Biochem.* 65: 368–387). These cell lines were immortalized with a temperature-sensitive simian virus (SV) 40 large T-antigen and exhibited a transformed phenotype at the permissive temperature (34° C.) when the T-antigen mutant was active. However, in contrast to osteosarcoma cells (Stein and Lian 1993 *Endocrine Rev.* 14: 424–442), the hOB cell lines were faithful to the proliferation/differentiation relationship at the nonpermissive temperature (>37° C.) when the T-antigen mutant is inactivated. The cell lines were seeded into 150 mm dishes at ~40,000 cells/cm² with growth medium [D-MEM/F-12 containing 10% (v/v) heat-inactivated fetal bovine serum (FBS), 1% (v/v) Penicillin-Streptomycin and 2 mM GlutaMAX-1] and incubated overnight at 34° C. The next day, the medium was removed, the cells were rinsed with phosphate-buffered saline (PBS), 20 ml of serum-free medium was added to the dishes [phenol red-free D-MEM/F-12 (Gibco/BRL) containing 0.25% (w/v) bovine serum albumin (BSA, Pentex crystallized, Bayer), 1% (v/v) Penicillin-Streptomycin, 2 mM GlutaMAX-1, 50 mM ascorbate-2-phosphate (Wako), and 10 nM menadione sodium bisulfite (vitamin $K_3$)], and the dishes were incubated at 39° C. for 24 hr. The next day, the medium was removed and the cells were treated at 39° C. for an additional 24 hr with 20 ml of fresh serum-free medium containing either vehicle (Control), 8 nM human parathyroid hormone 1–34 (PTH), 100 nM prostaglandin $E_2$ ($PGE_2$) or 0.1 nM human transforming growth factor-β1 (TGF-β1). PTH, $PGE_2$ and TGF-β1 are known osteogenic agents (Whitfield and Morley 1995 *Trends Pharmaceut. Sci.* 16:382–386; Jee and Ma 1997 *Bone* 21:297–304; Centrella et al. 1994 *Endocrine Rev.* 15:27–39). After the treatment period, the dishes were rinsed with PBS and total cellular RNA was isolated from the nontreated and treated cells using TRIzol according to the manufacturers instructions (GibcoBRL). RADE was then performed with the isolated RNA samples as above; the regulated gene fragments were identified, cloned and sequenced. These experiments identified a total of 82 differentially expressed genes. A BLAST (basic local alignment search tool) search of the public data bases was performed on the RADE-obtained gene fragments; one of the gene fragments was highly homologous to mouse SFRP-1. This gene fragment was identified during RADE using the following primer pair: 5'-AAGCTTTTTTTTTTA-3' (HT11A)3' end (reverse primer) and 5'-AAGCTTGATTGCC-3' (H-AP1) 5' end (forward primer), which sequences are SEQ ID NO 11 and SEQ ID NO 12, respectively. The expression and regulation of the gene fragment having homology to mouse cDNA SFRP-1 was confirmed by Northern blot analysis.

Example 2

Characterization of hOB SFRP

FIG. 1 depicts a summary of the RADE results. The hOB SFRP gene fragment (indicated by the arrows) was strongly up-regulated by $PGE_2$ in the proliferative-stage (hOB-03-C5) and maturation-stage (hOB-03-CE6) hOB cell lines and down-regulated by TGF-β1 in the pre-osteocytic (hOB-01-C1) cell line. Moreover, basal expression of this gene was dramatically increased in the pre-osteocytic cells, suggesting that hOB SFRP gene expression is linked to the osteoblast differentiation process.

Example 3

Sequence Analysis of the hOB SFRP Gene Fragment

The hOB SFRP gene fragment identified in Example 1, above, containing 276 base pair (bp) was cloned, sequenced, and a further subjected to a BLAST search of the public databases. This search revealed that this gene was homologous to two other previously identified cDNAs. Sequence alignment indicated that the hOB SFRP gene fragment shared 77% sequence identity to the 3'-end of mouse SFRP-1 gene (GeneBank™ Accession #U88566; Rattner et al. 1997 *Proc. Natl. Acad. Sci.* USA 94: 2859–2863). The hOB SFRP gene fragment also exhibited significant homology (87%) to the 3'-end of a related bovine cDNA called frizzled-related protein A (FrzA, GeneBank™ Accession #U85945). Additionally, the hOB SFRP gene fragment was very homologous to at least three expressed sequence tags (ESTs), human clone TM010 (GeneBank™ Accession #U54715), human CA11 tumor suppresser (GeneBank™ Accession #U69122) and a human infant brain EST (GeneBank™ Accession #H16753, H16861).

Example 4

Regulation of the hOB SFRP by Osteogenic Agents

In order to confirm the regulation of hOB SFRP gene expression by different osteogenic agents (i.e., the DNA fragment identified in Example 1, above), the hOB cell lines were treated with PTH, $PGE_2$, and TGF-β1; RNA was then isolated for Northern hybridizations. The results are shown in FIGS. 2 through 5. The experiments were performed as follows. The hOB cell lines were seeded into 150 mm dishes and treated as described in Example 1, except that polyA+ RNA was isolated from total cellular RNA using Oligotex mRNA maxi kits as described by the manufacturer (Qiagen). Northern blot analysis was performed using either the excised RADE hOB SFRP gene fragment, the cloned hOB SFRP gene fragment or the cloned full-length hOB SFRP cDNA as a $^{32}$P-labeled probe (as described in Bodine et al. 1996 *J. Bone Miner. Res.* 11: 806–819, which is incorporated herein). Each of these probes detected a 4.4–4.6 kb message in the hOB cells. Expression of the hOB SFRP mRNA was normalized to either glyceraldehyde phosphate dehydrogenase (GAPDH) mRNA or β-actin mRNA using the corresponding $^{32}$P-DNA probes. Treatment of the proliferative-stage hOB-03-C5 cells with 100 nM $PGE_2$ for 24 hr completely up-regulated the expression of a ~4.6 kilobase pair (kb) message (FIG. 2), confirming the regulation of this gene by $PGE_2$. When the cloned hOB SRFP gene fragment was used as a probe, a predominant mRNA of ~4.4 kb was observed in cells treated with $PGE_2$, confirming that this message is indeed the SFRP gene (FIG. 3). This mRNA corresponds in size to the transcript for the human FRP-1/SARP-2 gene (Finch et al. 1997 *Proc. Natl. Acad. Sci.* USA 94: 6770–6775; Melkonyan et al. 1997 *Proc. Natl. Acad. Sci.* USA 94: 13636–13641). Northern blot analysis also confirmed the up-regulation of hOB SFRP mRNA expression in maturation-stage hOB-03-CE6 cells treated with $PGE_2$ (FIG. 4). In addition, basal expression of this gene was elevated in pre-osteocytic hOB-01-C1 cells. This basal level expression was suppressed by 35% following treatment with 8 nM PTH. Furthermore, $PGE_2$ treatment of the maturation-stage hOB-03-CE6 cells elevated SFRP expression to the level that was expressed basely by the pre-osteocytic cells, implying that up-regulation of SFRP by $PGE_2$ in the osteoblastic cells is related to the enhancement of cellular differentiation. Lastly, treatment of the pre-osteocytic hOB-01-C1 cells with 100 pM TGF-β1 for 24 hr suppressed hOB SFRP mRNA levels by 80% (FIG. 5).

To confirm that hOB SFRP message levels change with increasing cellular differentiation, total RNA was isolated from the pre-osteoblastic hOB-03-C5 cells, the mature osteoblastic hOB-03-CE6 cells, the pre-osteocytic hOB-01-C1 cells and the mature osteocytic hOB-05-T1 cells. Basal SFRP mRNA levels were then measured by TaqMan quantitative RT-PCR. When compared to the hOB-03-C5 cells, basal SFRP message levels increased about 4-fold in the hOB-03-CE6 cells and about 23-fold in the hOB-01-C1 cells. On the other hand, SFRP mRNA levels declined to about 0.5-fold in the hOB-05-T1 cells. Thus, of the cells in the osteoblast lineage, the pre-osteocyte appears to express the highest levels of hOB SFRP message.

Example 5

Kinetics of hOB SFRP Expression

Proliferative hOB-03-C5 cells were seeded into 150 mm dishes and treated with increasing concentrations of $PGE_2$ for 24 hr or with 100 nM $PGE_2$ for varying lengths of time as described in Example 1. PolyA+ RNA Northern blot analysis was performed with the excised RADE hOB SFRP 276 bp gene fragment or a cloned 1.1 kb hOB SRFP gene fragment as a $^{32}P$-labeled probe. Treatment of the proliferative-stage hOB-03-C5 cells with increasing concentrations of $PGE_2$ up-regulated hOB SFRP mRNA expression in a dose-dependent manner with an $EC_{50}$ of approximately 8 nM. Likewise, treatment of the mature hOB-03-CE6 cells with increasing concentrations of $PGE_2$ also up-regulated hOB SFRP mRNA levels in a dose-dependent manner, although the $EC_{50}$ of $PGE_2$ for this response was about 10-times higher than in the hOB-03-C5 cells.

Treatment of the hOB-03-C5 cells with 100 nM $PGE_2$ for 2 to 24 hr up-regulated hOB SFRP mRNA expression in a time-dependent manner. A significant increase in SFRP gene expression was observed after 2 to 4 hr of treatment, and the steady-state mRNA levels continued to increase up to 24 hr after the addition of $PGE_2$ to the cell culture medium. These results suggest that SFRP may be a late-response gene to $PGE_2$ treatment of the hOB cells, and implies that it may be under the secondary control of another gene product. Similar results were also obtained with the mature hOB-03-CE6 cells, although the fold-increase in expression of the hOB SFRP message was not as great as it was in the hOB-03-C5.

In a similar manner, the hOB-01-C1 cells were seeded into 100 mm dishes and treated for 24 hr with increasing concentrations of TGF-β1. Total RNA was then isolated from the cells, and hOB SFRP mRNA was measured by TaqMan quantitative RT-PCR. TGF-β1 suppressed SFRP gene expression by approximately 70% in a dose-dependent manner with an $IC_{50}$ of about 4 pM.

In addition to $PGE_2$, treatment of either the hOB-03-C5 cells or the hOB-03-CE6 cells with interleukin (IL)-1β, 9-cis-retinoic acid or all-trans-retinoic acid also increases hOB SFRP mRNA levels. On the other hand, as with TGF-β1, treatment of various hOB cell lines with PTH, bone morphogenetic protein (BMP)-2, insulin-like growth factor (IGF)-I, 17β-estradiol (17β-$E_2$), vitamin $D_3$ ($VD_3$), dexamethasone (Dex), or fetal bovine serum (FBS) suppresses hOB SFRP message expression. Overall, there is a good (albeit imperfect) correlation between the abilities of these various agents to either increase or decrease hOB SFRP expression, and their ability to either enhance or suppress osteoblast/osteocyte apoptosis (see for example Manolagas 2000 Endocrine Reviews 21: 115–137).

Example 6

Tissue Distribution of hOB SFRP

Figure 6:
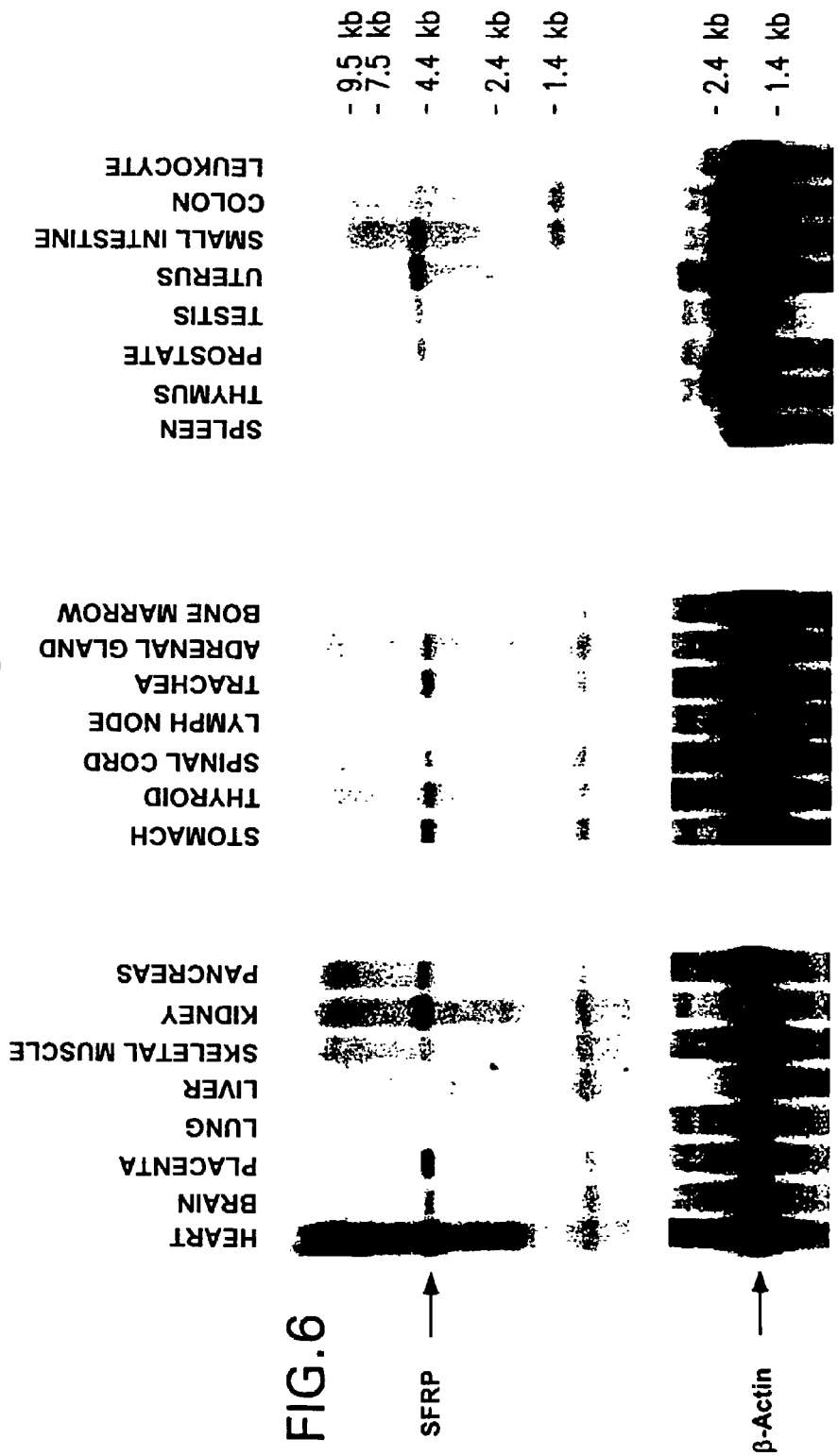
FIG. 6 shows an autoradiogram of a Northern blot of poly A+ RNA isolated from 23 different human tissues. In this experiment, both the excised hOB SFRP RADE gene fragment and a cloned beta-Actin cDNA were used as probes. The arrow points to the hOB SFRP mRNA that is highly expressed in heart and kidney, moderately expressed in placenta and uterus, expressed at lower levels in brain, pancreas and other tissues, but not expressed in thymus and lymphocytes.

In order to determine the tissue distribution for the expression of the hOB SFRP gene, multiple human tissue poly(A)+ RNA Northern blots (obtained from Clonetech) were probed with the excised RADE hOB SFRP gene fragment as described in Example 4. When the RADE fragment was used to probe the poly (A)+ RNA Northern blots, a ~4.4 kb transcript was expressed by several tissues (FIG. 6). When these results were normalized to β-actin, SFRP expression was ranked as follows:

Kidney>heart>placenta>liver=skeletal muscle=stomach= thyroid gland>adrenal gland=testis=uterus=small intestine=pancreas=brain>trachea=spinal cord=prostate= colon>spleen>lung=lymph node=bone marrow;

No expression was observed in thymus and peripheral blood lymphocytes. This expression pattern is similar to the human FRP-1/SARP-2 gene (Finch et al. 1997 *Proc. Natl. Acad. Sci.* USA 94: 6770–6775; Melkonyan et al. 1997 *Proc. Natl. Acad. Sci.* USA 94: 13636–13641).

Example 7

Distribution of SFRP in Osteoblast Cell Lines

In addition to the hOB cell lines from which SFRP was initially identified, additional in vitro human osteoblast models were examined for the presence of the gene. SaOS-2 human osteosarcoma osteoblast-like cells were obtained from the American Type-Culture Collection (ATCC) and were cultured at 37° C. in McCoy's 5A Modified medium containing 10% FBS, 1% (v/v) Penicillin-Streptomycin and 2 mM GlutaMAX-1. Likewise, explant cultures of normal human osteoblasts (hOBs) were established from cancellous bone chips as previously described (Bodine et al. 1996 J. Bone Miner. Res. 11: 806–819, which is incorporated herein by reference). The cells were then seeded into 150 mm dishes and treated as described in Examples 1 and 4, except that the cells were incubated at 37° C. instead of 39° C. PolyA+ RNA Northern blot analysis was performed using the cloned 1.1 kb hOB SRFP gene fragment as a $^{32}P$-label). SaOS-2 cells expressed relatively low basal levels of SFRP mRNA which was not regulated by treatment with either PTH, $PGE_2$ or TGF-β1 (FIG. 7). It was difficult to quantify expression of this gene in these cells, since the level of expression was low. In contrast, normal hOB cells expressed higher basal levels of SFRP message, and treatment of the cells with 100 nM $PGE_2$ for 24 hr appeared to slightly up-regulate the steady-state levels of this mRNA (~1.3-fold). TaqMan quantitative RT-PCR analysis of these RNA samples indicated that $PGE_2$ upregulated SFRP 10-fold in the hOB cells. Due to the low basal level expression in osteosarcoma cells, these cells may not be satisfactory in vitro models to study the regulation of the SFRP gene. Since the gene is expressed and regulated by $PGE_2$ in cultures of normal human osteoblasts, the use of the hOB cell lines described in the present invention is validated for in vitro osteoblast models. Northern blot analysis and RT-PCR of total RNA isolated from a human giant cell tumor of bone failed to detect expression of the hOB SFRP mRNA in this tissue. These results suggest that osteoclast-like cells may not express this gene.

Example 8

Isolation of Full Length hOB SFRP cDNA

Figure 8:
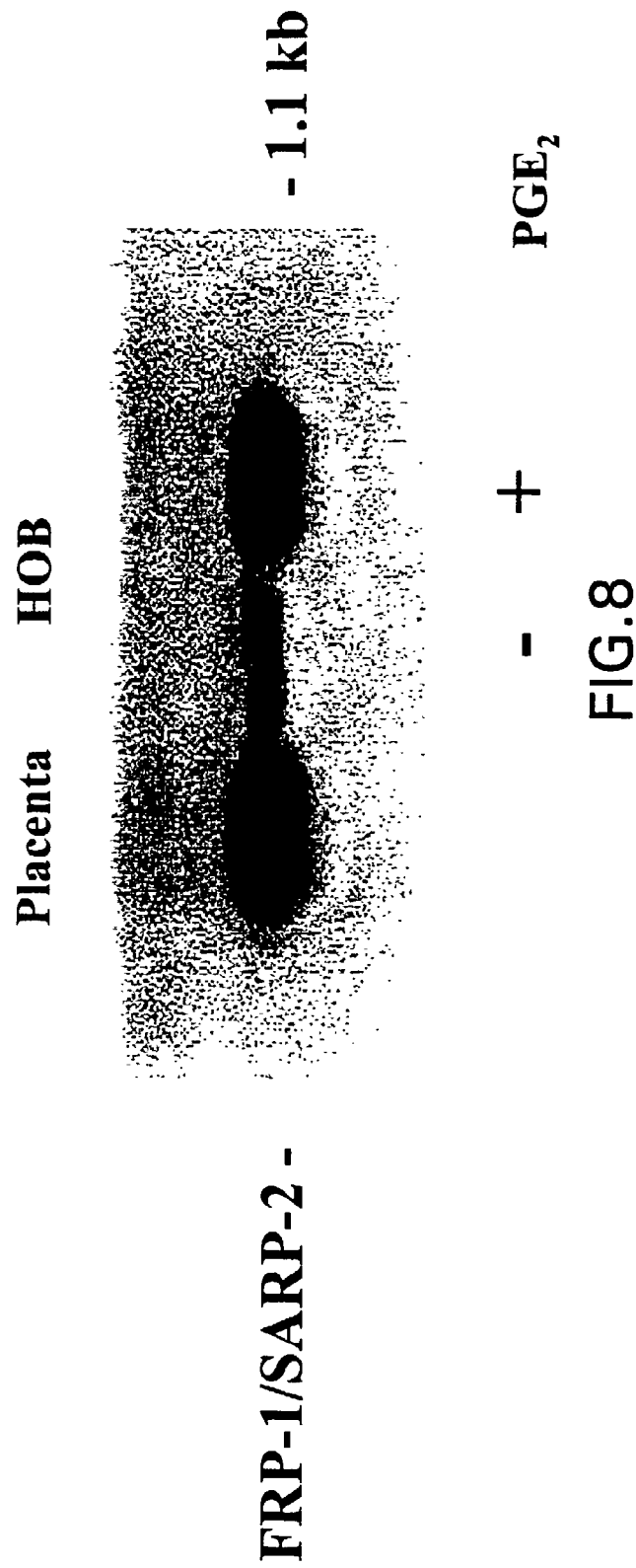
FIG. 8 shows an autoradiogram of a Southern blot of reverse transcriptase (RT)-PCR products of total RNA isolated from either human placenta or hOB-03-CE6 cells after treatment with control or PGE$_2$ for 24 hr. RT-PCR was performed with oligonucleotide primers that were specific for human FRP-1/SARP-2, and the Southern blot was hybridized with an internal oligonucleotide probe specific for human FRP-1/SARP-2. The expected size for this RT-PCR product was 1.1 kb. The results shown that (as expected) placenta expresses FRP-1/SARP-2 mRNA, and that PGE$_2$ treatment of the hOB-03-CE6 cells strongly upregulates the expression of this message.

Since the cloned hOB SFRP gene fragment from RADE was identical to several human ESTs, an analysis of the EST database was performed in order to assemble the full-length cDNA for the hOB gene. This analysis suggested that the hOB SFRP was in fact the known human gene, FRP-1 (also called the secreted apoptisis-related protein-2 or SARP-2). Based on this analysis, and the observation that the mouse SFRP-1 gene is apparently homologous to the human FRP-1 gene and the human SARP-2 gene (Rattner et al. 1997 Proc. Natl. Acad. Sci. USA 94: 2859–2863; Finch et al. 1997 Proc. Natl. Acad. Sci. USA 94: 6770–6775; Melkonyan et al. 1997 Proc. Natl. Acad. Sci. USA 94: 13636–13641), an RT-PCR-based strategy was designed to obtain the full-length 1.1 kb hOB SFRP cDNA from both human placenta RNA and $PGE_2$-treated hOB-03-CE6 cell RNA. RT-PCR was performed using 1 µg of total RNA, primers that spanned the coding region of hFRP-1/SARP-2 (forward primer: 5'-GCTGGGGACTGCGCCTTTTGT-3' SEQ ID NO 13; reverse primer: 5'-CCTGCCCCCGGGAGAATCACTTA-3' SEQ ID NO 14), 35 cycles of PCR, and the Advantage-GC PCR kit (Clonetech) according to the manufacturer's instructions. In order to detect expression of the mRNA, a Southern blot analysis was performed with the RT-PCR products using a $^{32}$P-oligonucleotide probe which specifically hybridized to bases 501 to 530 of the hFRP-1/hSARP-2 coding region (refer to Bodine et al. 1997 J. Cell. Biochem. 65: 368–387 for experimental details concerning RT-PCR and Southern hybridizations). Full-length 1.1 kb cDNA for the hOB SFRP was isolated and was up-regulated by 100 nM $PGE_2$-treatment of the hOB-03-CE6 cells for 24 hr (FIG. 8). Likewise, RT-PCR of total RNA isolated from hOB-03-C5 cells treated with $PGE_2$ identified a 2.2 kb cDNA which spanned from the 5'-region of the hFRP-1/SARP-2 cDNA to the 276 bp RADE fragment at the 3'-end. These cDNA fragments were cloned into either the pcDNA3.1 (Invitrogen) mammalian expression vector (1.1 kb cDNA) or the TA (Invitrogen) cloning vector (2.2 kb cDNA) and sequenced. Sequence analysis of the hOB SFRP 1.1 kb (SEQ. ID. NO.: 1) and 2.2 kb cDNAs enabled the assembly of a 2.6 kb cDNA which included the transcription start site at the 5'-end and the RADE fragment at the 3'-end. A BLAST search of the public databases using the 1.1 kb cDNA indicated that it essentially was identical to human FRP-1/SARP-2. The deduced amino acid sequence of the coding region of the SFRP cDNA is shown in SEQ. ID. NO. 2. The sequence contains one amino acid difference from the published sequence for human SARP-2: alanine 174 instead of proline at this position (Melkonyan et al. 1997 Proc. Natl. Acad. Sci. USA 94: 13636–13641).

Example 9

Characterization of the Apoptotic Activity of hOB

Since the cloned full-length hOB SFRP gene was identical to human SFRP-1/FRP-1/SARP-2, the biological role of this gene in the hOB was investigated to determine whether the gene product regulated hOB cell viability and Wnt signaling (FIGS. 9–16).

Figure 9:
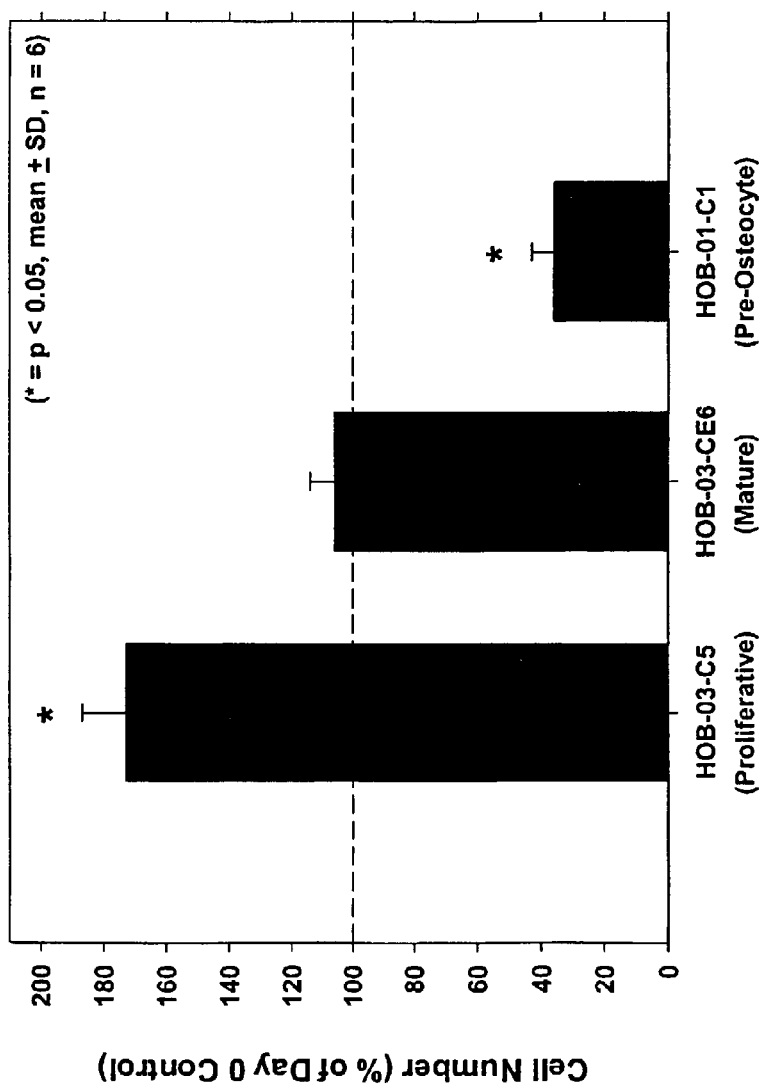
FIG. 9 shows the results of a cell viability experiment with the hOB-03-C5, hOB-03-CE6 and hOB-01-C1 cells using the Coulter cell counter. The results are presented as the % relative to the day 0 control (i.e., ~200,000 cells per well of a 6 well plate). The results of this experiment indicate that the hOB-03-C5 cells proliferate slowly at 39° C. in serum-containing medium, while the hOB-03-CE6 cells stop dividing but are viable for the 6 day incubation. In contrast, the hOB-01-C1 cells undergo accelerated cell death, which correlates with the high basal expression of hOB SFRP mRNA in these cells.

As shown in FIG. 9, hOB cells were seeded at 200,000 cells/well into 6-well dishes and incubated at 34° C. The next day, one set of plates were rinsed with PBS, trypsinized, and baseline cell number (and mean cell volume) was determined with a Coulter Multisizer as previously described in Bodine et al. 1996 J. Bone Miner. Res. 11: 806–819, which is incorporated herein by reference. The other set of plates was placed at the non-permissive temperature of 39° C., and cell number was determined 6 days later (the medium was changed on day 3). The hOB-03-C5 cells, which are in the proliferative-stage of osteoblast differentiation, divided slowly at 39° C. and cell number increased by 60 to 80% after 6 days; this rate of cell division was similar to explant cultures of normal hOB cells (Bodine et al. 1996 Endocrinology 137: 4592–4604). In contrast, the maturation-stage hOB-03-CE6 cells stopped dividing at the non-permissive temperature and cell number remained constant, while the pre-osteocytic hOB-01-C1 cells slowly died at 39° C. such that fewer than 40% of the cells remained alive after 6 days. As noted previously, overexpression of SARP-2 in MCF-7 breast cancer cells accelerated the rate of cell death. Consistent with this observation, and as shown in FIGS. 1, 4 and 5, basal SFRP-1/FRP-1/SARP-2 mRNA expression dramatically increased in the pre-osteocyte hOB-01-C1 cells when compared to the proliferative hOB-03-C5 and mature hOB-03-CE6 cell lines.

Figure 10A:
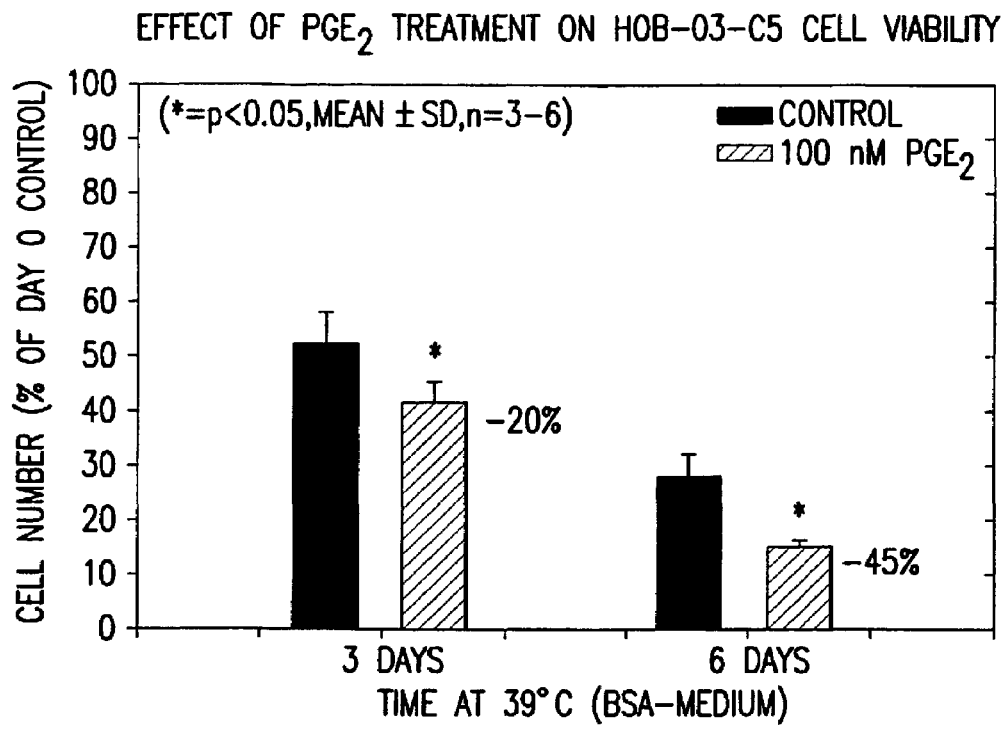
FIG. 10 shows the results of a cell viability experiment with the hOB-03-C5 cells (panel A), hOB-03-CE6 cells (panel B) and hOB-01-C1 cells (panel C) using the Coulter cell counter. For these experiments, the cells were treated with either control or $PGE_2$ (panels A & B) or control and TGF-β1 (panel C) in serum-free medium at 39° C. for 3 or 6 days. The results are presented as the % relative to the day 0 control (i.e., ~200,000 cells per well of a 6 well plate). The results of this experiment indicate that hOB cell viability declines over time in serum-free medium. In addition, for the hOB-03-C5 and hOB-03-CE6 cells, this rate of decline is accelerated by treatment with $PGE_2$. This enhanced rate of cell death correlates with the upregulation of hOB SFRP mRNA levels in these cells following $PGE_2$ treatment. In contrast, treatment of the hOB-01-C1 cells with TGF-β1, which downregulates hOB SFRP message levels, increases cell viability.
Figure 10B:
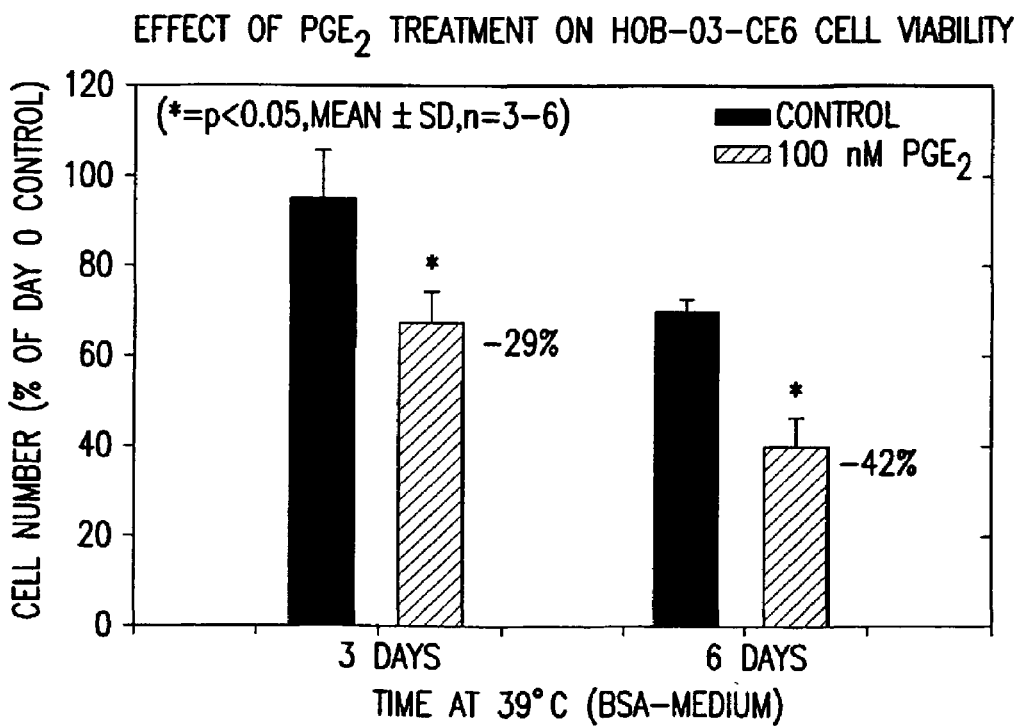
Figure 10C:
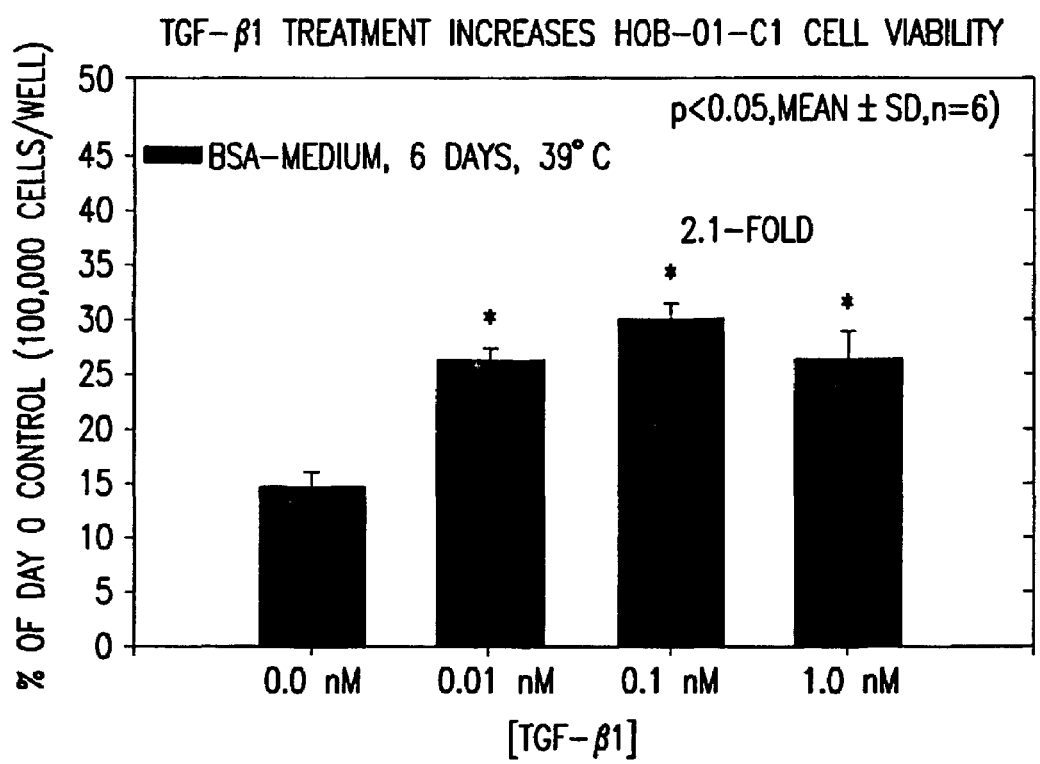
Figure 11A:
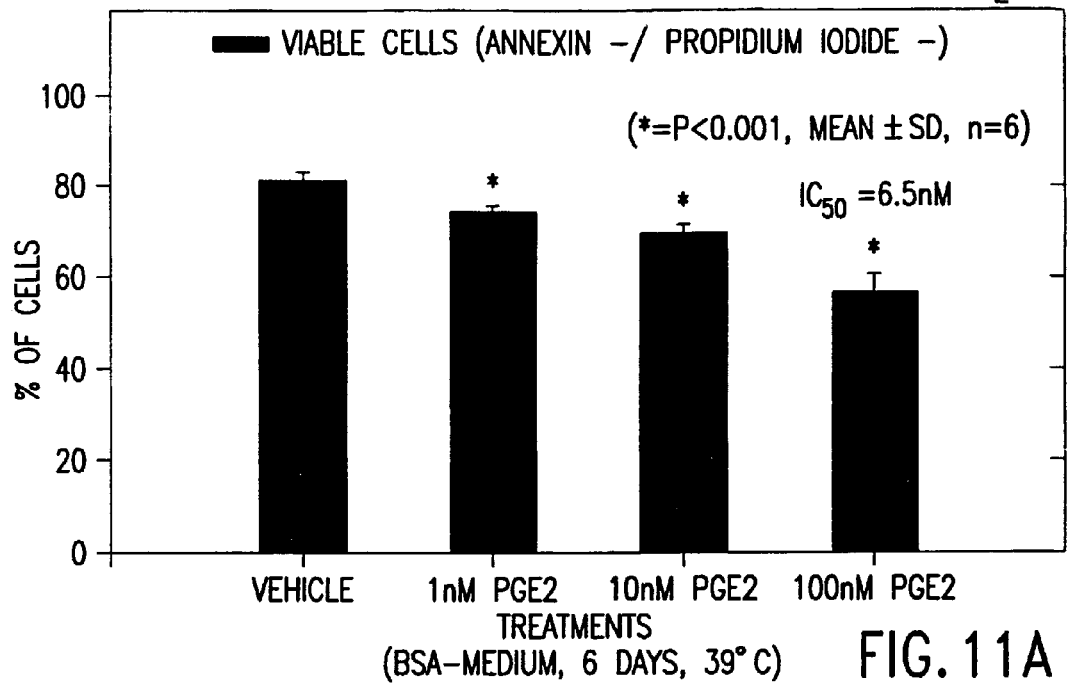
FIG. 11 shows that treatment of hOB-03-C5 cells with $PGE_2$ induces apoptosis or programmed cell death. Apoptosis was measured by flow cytometry using annexin V-FITC. Panel A shows that the number of viable cells, which do not stain with either annexin V or propidium iodide (a stain for necrotic cells), declines with increasing $PGE_2$ concentrations. In contrast, panel B shows that the number of apoptotic cells, which stain with annexin V but not propidium iodide, increases with increasing $PGE_2$ concentrations. Similarly, panel C shows that the number of necrotic cells, which stain with both annexin V and propidium iodide, increases with increasing $PGE_2$ concentrations.
Figure 11B:
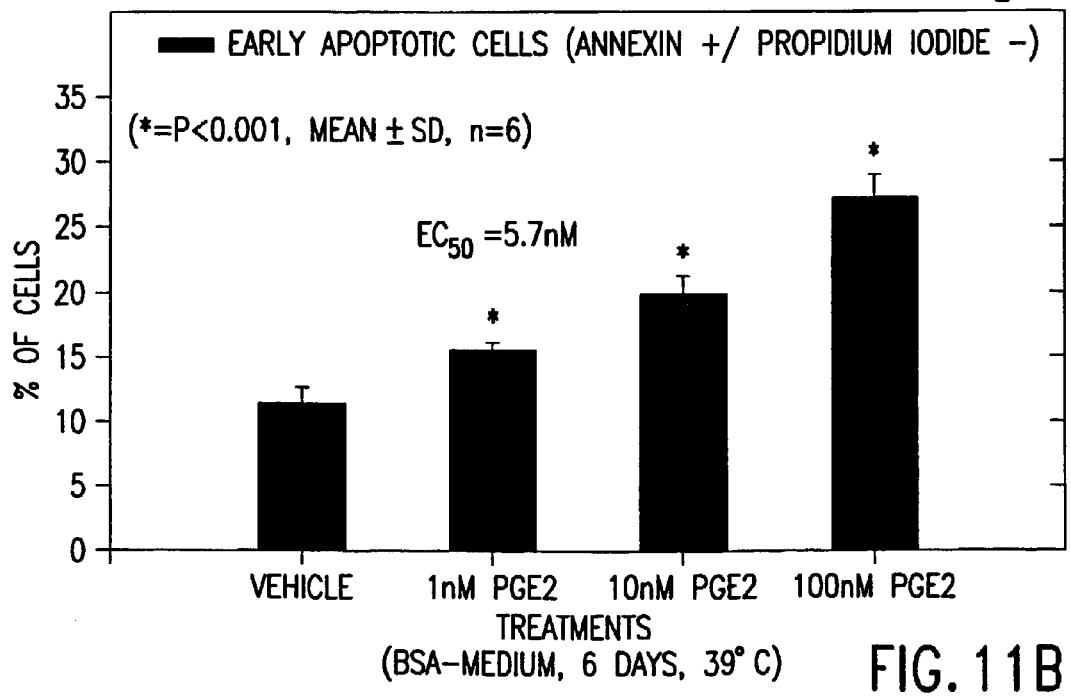
Figure 11C:
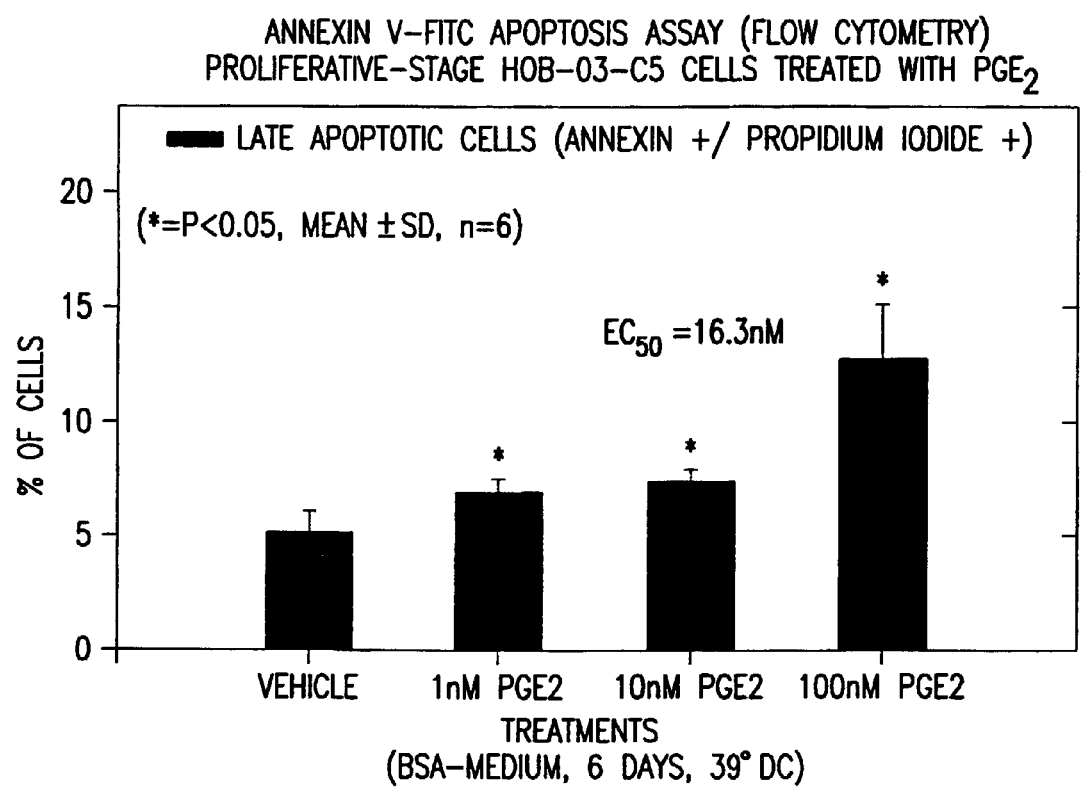

The hypothesis that up-regulation of SFRP-1/FRP-1/SARP-2 gene expression accelerates hOB cell death, while down-regulation of SFRP-1/FRP-1/SARP-2 gene expression suppresses cell death, was next examined. These results are depicted in FIG. 10. hOB-03-C5, hOB-03-CE6 or hOB-01-C1 cells were seeded with growth medium at about 200,000 cells per well into 6-well plates and incubated at 34° C. overnight. The next day, the 6-well plates were rinsed with PBS, placed in BSA-medium, and treated at 39° C. in the absence or presence of either 100 nM $PGE_2$ (in order to up-regulate SFRP-1/FRP-1/SARP-2 steady-state mRNA levels; panels A & B), or 0.01–1.0 nM TGF-β1 (in order to down-regulate SFRP-1/FRP-1/SARP-2 message levels; panel C). Incubating cells in serum-free medium is a common method to induce apoptosis (Melkonyan et al. 1997 Proc. Natl. Acad. Sci. USA 94: 13636–13641), and the hOB-03-C5, hOB-03-CE6 and hOB-01-C1 cell lines all stopped dividing and gradually died under these conditions. However, the rate of cell death was significantly accelerated when the hOB-03-C5 and hOB-03-CE6 cells were treated with $PGE_2$, such that over 40% fewer cells remained alive after 6-days of treatment. In contrast, treatment of the hOB-01-C1 cells with TGF-β1 increased cell viability about 2-fold in a dose-dependent manner. Treatment of the cells with $PGE_2$ not only accelerated cell death, but also significantly reduced the mean cell volume by 10 to 20%. This observation was consistent with the induction of apoptosis, which is known to result in cytoplasmic blebbing, the loss of water and a decrease in cell volume (Mesner and Kaufmann 1997 in Advances in Pharmacology, vol. 41, pp. 57–88). Also consistent with the induction of apoptosis, $PGE_2$-treatment of the hOB-03-C5 cells resulted in the generation of histone-associated DNA fragments. Finally, treatment of the hOB-03-C5 cells with $PGE_2$ increased annexin V (a specific marker for apoptosis) binding to the cell as measured by flow cytometry (FIG. 11).

Example 10

Reversal of Cell Death Induction

Figure 12A:
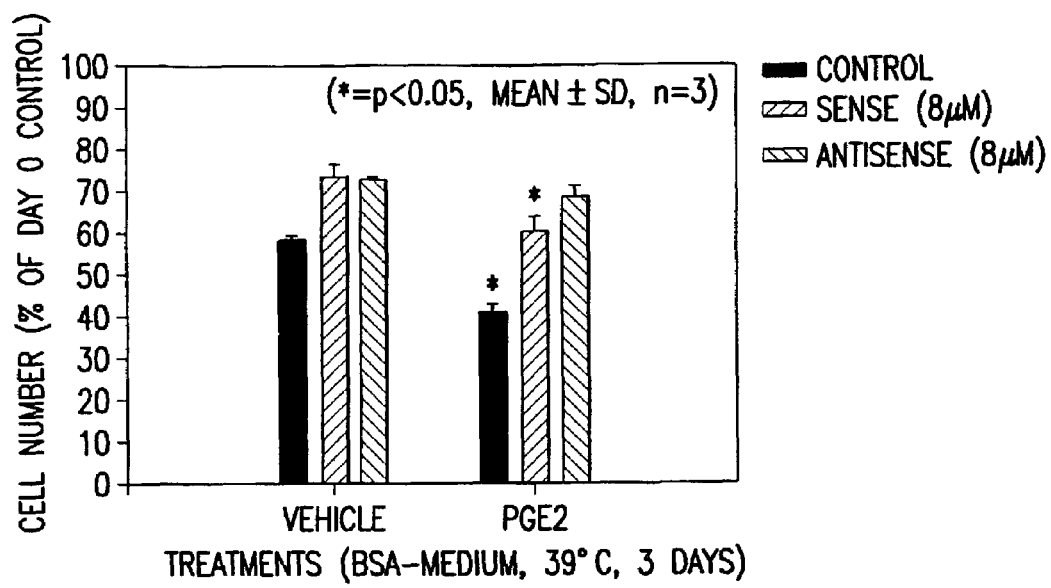
FIG. 12 shows the results of another cell viability experiment with the hOB-03-C5 cells (panel A) and hOB-03-CE6 cells (panel B) using the Coulter cell counter. These experiments were performed in a similar manner to the ones depicted in FIG. 10. However, for these experiments, the cells were co-treated with either vehicle control (i.e., 0.1% ethanol) or $PGE_2$ in the absence or presence of sense (control) or antisense initiation-site directed phosphorothioate oligonucleotides to human SARP-2. The results are presented as either the % relative to the day 0 control (i.e., ~200,000 cells per well of a 6 well plate) or as the % relative to the vehicle treated control. The results of this experiment indicate that co-treatment of the hOB cells with the antisense oligonucleotide to SARP-2 reverses the ability of $PGE_2$ to accelerate the rate of cell death, while co-treatment with the sense (control) oligonucleotide as no effect on this process.
Figure 12B:
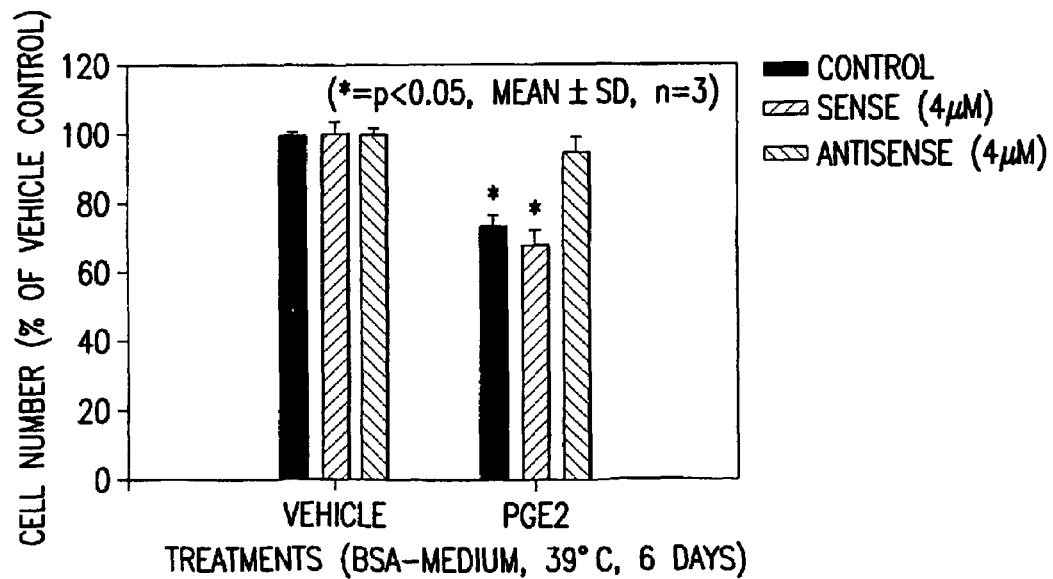

Reversal of cell death using an antisense oligonucleotide to SFRP-1/FRP-1/SARP-2 is demonstrated in FIG. 12 using hOB-03-C5 and hOB-03-CE6. These experiments were performed in a similar manner to the ones depicted in FIG. 10.

However, for these experiments, the cells were co-treated with either vehicle control (i.e., 0.1% ethanol) or PGE$_2$ in the absence or presence of sense (control) or antisense initiation-site directed phosphorothioate oligonucleotides to human SARP-2. The results are presented as either the % relative to the day 0 control (i.e., ~200,000 cells per well of a 6 well plate) or as the % relative to the vehicle treated control. The results of this experiment indicate that co-treatment of the hOB cells with the antisense oligonucleotide to SARP-2 reversed the ability of PGE$_2$ to accelerate the rate of cell death, while co-treatment with the sense (control) oligonucleotide has no effect on this process. In addition, co-treatment of the cells with PGE$_2$ and an antipeptide antibody to SARP-2 blocked the ability of PGE$_2$ to induce hOB cell death. The sequences for the sense and antisense oligonucleotides to human SFRP-1/SARP-2 are as follows:

Sense: 5'-GGCATGGGCATCGGGCGC-3' (SEQ ID NO. 15)

Antisense: 5'-GCGCCCGATGCCCATGCC-3' (SEQ ID NO. 16)

Example 11

Overexpression of SFRP Accelerates hOB Cell Death

Figure 13A:
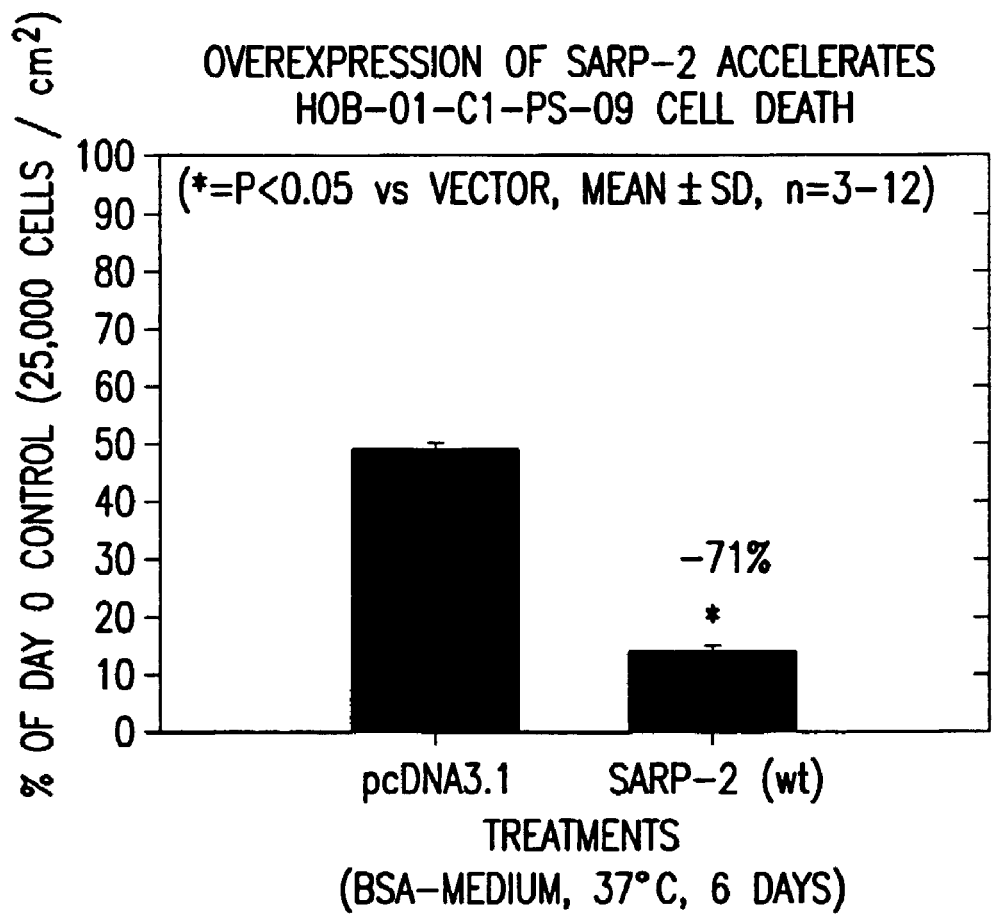
FIG. 13 shows the results of a cell viability experiment with the hOB-01-C1-PS-09 cells using the Coulter cell counter (panel A). For these experiments, the cells were stably transfected with either an hOB SFRP cDNA (i.e., SFRP-1/FRP-1/SARP-2) mammalian expression plasmid or the empty vector (i.e., pcDNA3.1). The results are presented as the % of the day 0 control cells. The results of this experiment indicates that overexpression of hOB SFRP/SFRP-1/FRP-1/SARP-2 by the hOB cells accelerates the rate of cell death when compared to the empty vector which has no effect on this process. Panel B shows the results of a Northern hybridization of poly A+ RNA isolated from either the empty vector cells (V) or the SARP-2 overexpressing cells (S). This analysis demonstrates that the SARP-2 cells express substantially more SFRP-1/FRP-1/SARP-2 mRNA than the vector cells.
Figure 13B:
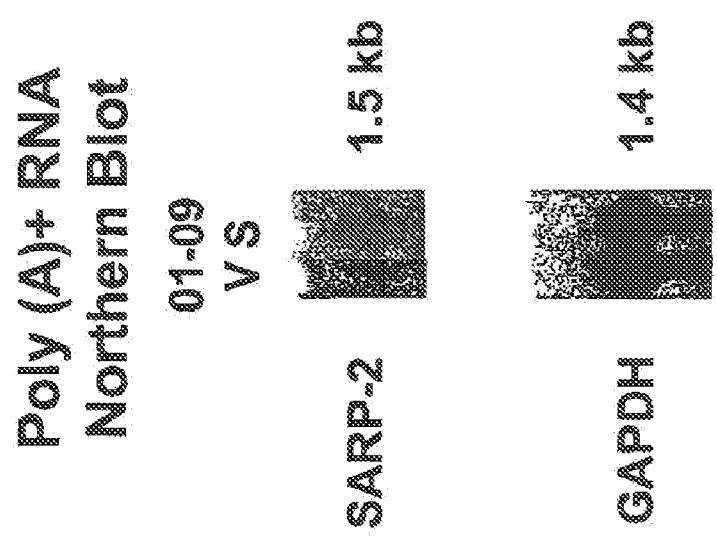

FIG. 13 shows the results of a cell viability experiment with the hOB-01-C1-PS-09 cells using the Coulter cell counter. For these experiments, the cells were stably transfected with either an hOB SFRP cDNA (i.e., SFRP-1/FRP-1/SARP-2) mammalian expression plasmid or the empty vector (i.e., pcDNA3.1, which is obtained from Invitrogen of Carlsbad, Calif.). Standard cloning techniques were used (See Ausubel et al. 1997 Short Protocols in M<olecular Biology, 3$^{rd}$ edition, Wiley {New York}). The results are presented as the % of the day 0 control cells. The results of this experiment indicated that overexpression of SFRP-1/FRP-1/SARP-2 by the hOB cells accelerates the rate of cell death when compared to the empty vector which has no effect on this process. Autoradiograms of a Northern blot of total RNA isolated from the empty vector (v) or SFRP(S) expressing cells demonstrated that the hOB cells overexpressed the SFRP gene as expected. In addition, TaqMan quantitative Rt-PCR analysis indicated that the SFRP overexpressing cells expressed 5–6 times more SFRP mRNA than the empty-vector expressing cell.

Figure 14A:
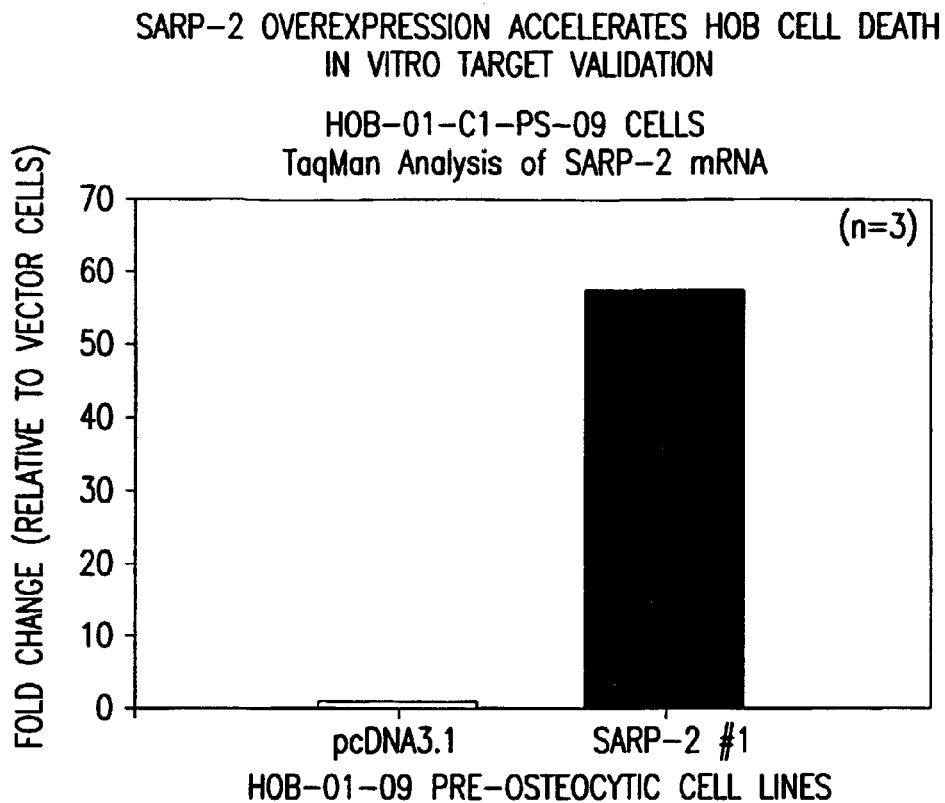
FIG. 14 shows the results of another cell viability experiment performed with the empty vector expressing hOB-01-C1-PS-09 cells (pcDNA3.1) and a subclone of the SFRP-1/FRP-1/SARP-2 overexpressing cells (SARP-2 Clone #1). Panel A shows the results of a TaqMan quantitative RT-PCR analysis of RNA isolated from the cells. This analysis indicates that the SARP-2 Clone #1 cells express 50–60 times more human SFRP-1/FRP-1/SARP-2 mRNA than the empty vector expressing cells. Likewise, as shown in panel B, the SARP-2 Clone #1 cells die at a rate that is 3-times faster than the empty vector control cells using the Coulter cell counter to measure cell number.
Figure 14B:
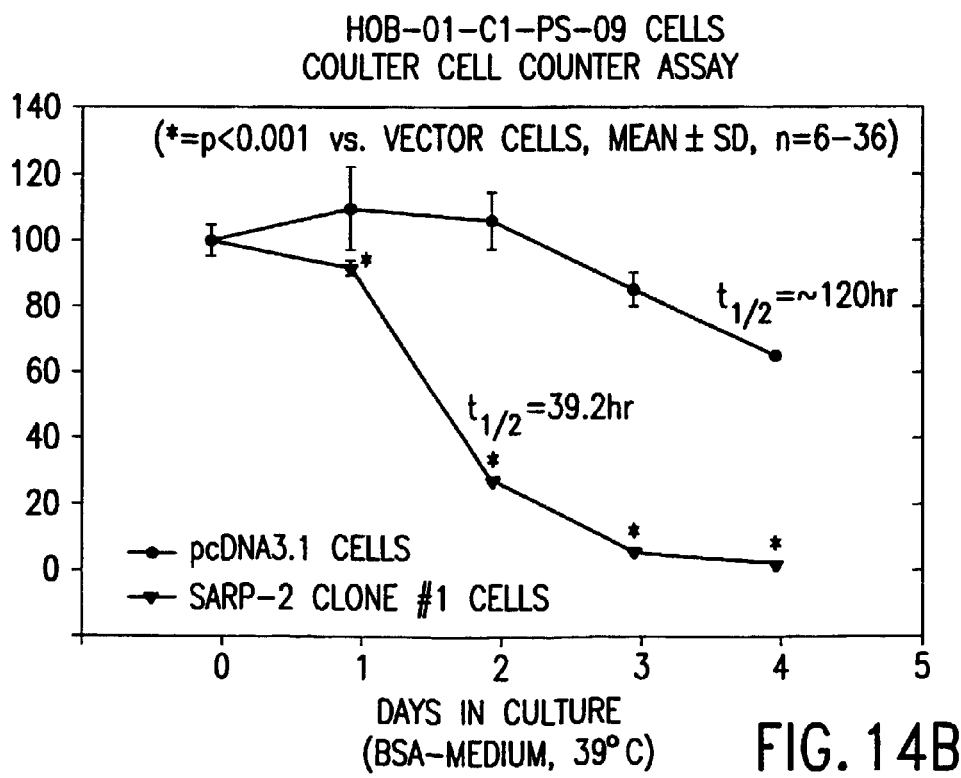

In order to improve the rate of cell death that was induced by SFRP-1/FRP-1/SARP-2, the overexpressing hOB-01-C1-PS-09 were subcloned and characterized (FIG. 14). TaqMan quantitative RT-PCR analysis indicated that one subclone (SARP-2 Clone #1) expressed 50–60-times more SFRP-1/FRP-1/SARP-2 mRNA than the pcDNA3.1 (empty vector) expressing cells. Likewise, the SARP-2 Clone #1 cells died at greatly accelerated rate ($t_{1/2}$=39.2 hr) in BSA-medium when compared to the empty vector expressing cells ($t_{1/2}$=~120 hr).

Example 12

Effect of hOB SFRP on Wnt Activity

Figure 15:
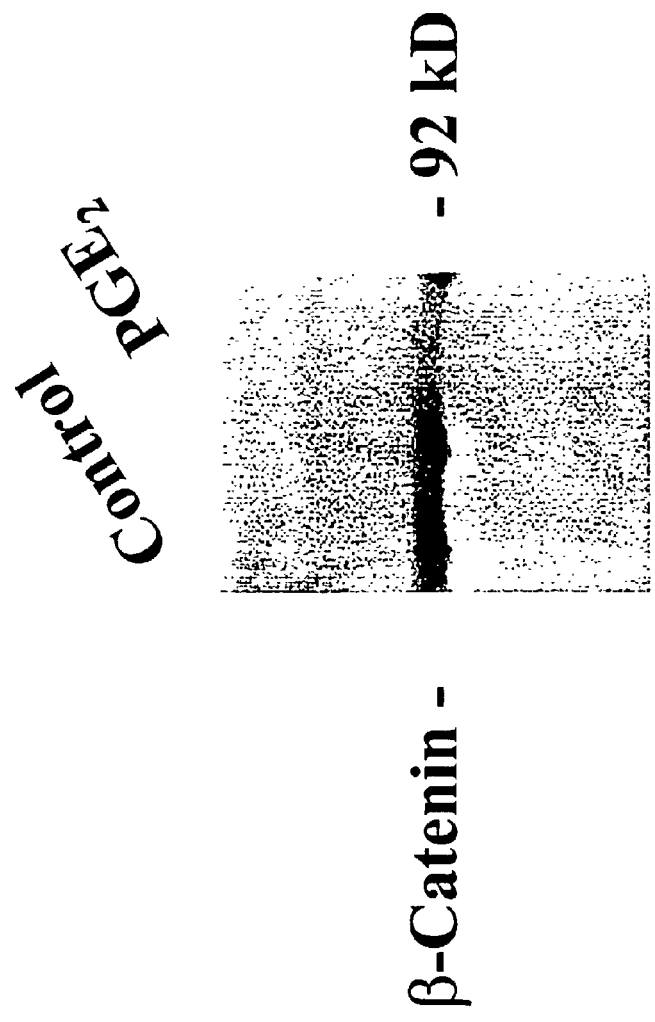
FIG. 15 is an autoradiogram of a Western blot of whole cell extracts isolated from hOB-03-CE6 cells treated with either control or $PGE_2$ for 24 hr. The immunoblot was probed with a monoclonal antibody to β-catenin, which has a molecular weight of 92,000. The results show that treatment of the hOB cells with $PGE_2$ downregulates β-catenin levels, which is consistent with an antagonism of the Wnt signaling pathway by hOB SFRP/SFRP-1/FRP-1/SARP-2.
Figure 16A:
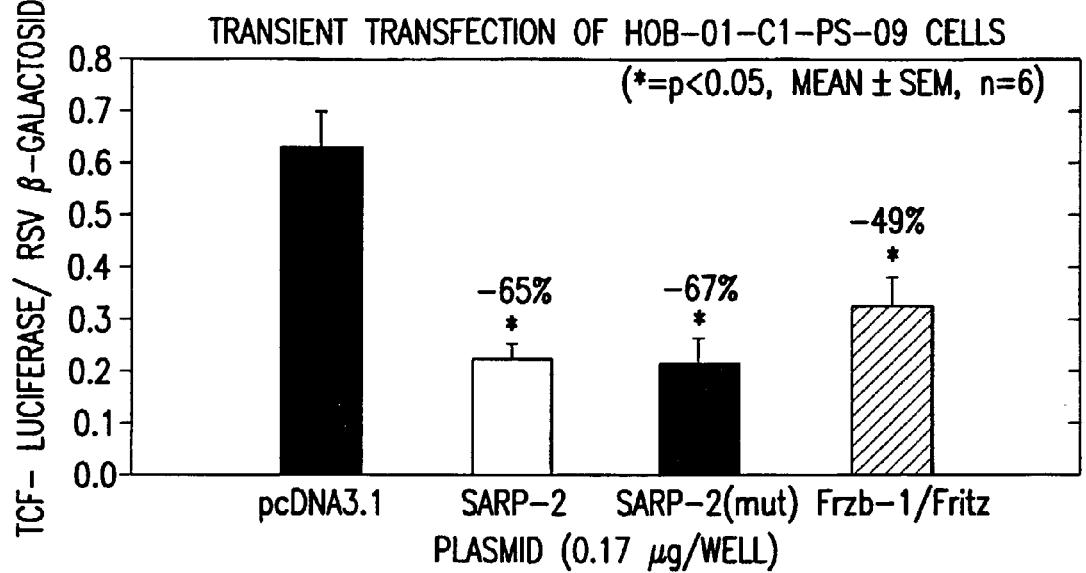
FIG. 16 shows the results of a transient transfection experiment with the hOB-01-C1-PS-09 cells (panel A) and hOB-02-C1-PS-02 cells (panel B). The results show that transfection of either human [h] or rat [r] SARP-2 or human Frzb-1 expression plasmids downregulates Wnt signaling (when compared to the pcDNA3.1 empty vector control) in the hOB cells as measured by the TCF-luciferase reporter gene assay. This assay is an authentic measurement of Wnt signaling and β-catenin nuclear activity.
Figure 16B:
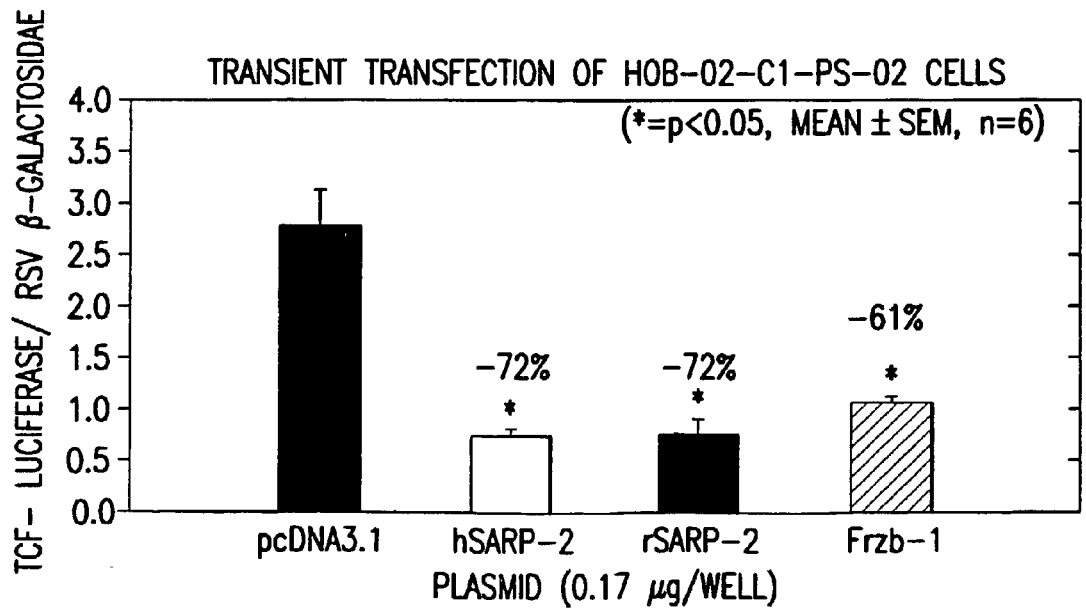

In order to determine if the up-regulation of SFRP-1/FRP-1/SARP-2 gene expression results in an antagonism of the Wnt signaling pathway, hOB-03-CE6 cells were treated with PGE$_2$ and the resulting cells probed with β-catenin monoclonal antibody. Overexpression of Wnt proteins in cells up-regulates a signaling protein known as β-catenin (reviewed in Moon et al. 1997 Cell 88: 725–728; Barth et al. 1997 Curr. Opin. Cell Biol. 9: 683–690; and Nusse 1997 Cell 89: 321–323). Moreover, overexpression of SFRP-1/FRP-1/SARP-2 in MCF-7 cells down-regulated β-catenin levels, which is consistent with an antagonism of Wnt activity (Melkonyan et al. 1997 Proc. Natl. Acad. Sci. USA 94: 13636–13641). Therefore, hOB-03-CE6 cells were plated and treated with PGE$_2$ as described in Example 1, except that total cellular protein was extracted and a Western blot analysis for β-catenin was performed using a monoclonal antibody to the protein (Transduction Laboratories) as previously described (Bodine et al. 1996 Endocrinology 137: 4592–4604; Melkonyan et al. 1997 Proc. Natl. Acad. Sci. USA 94: 13636–13641). Consistent with up-regulation of SFRP-1/FRP-1/SARP-2 steady-state mRNA levels, treatment of hOB-03-CE6 cells with 100 nM PGE$_2$ for 24 hr down-regulated β-catenin protein levels indicating an antagonism of Wnt activity (FIG. 15). In addition, cotransfecting SFRP-1/FRP-1/SARP-2 cDNA into either hOB-01-C1-PS-09 or hOB-02-C1-PS-02 cells down-regulated TCF-luciferase expression which is an authentic measurement of Wnt signaling and β-catenin nuclear activity (FIG. 16) (e.g., Bafico et al. 1999 J. Biol. Chem. 274: 16180–16187). Both human and rat SFRP-1/FRP-1/SARP-2, as well as human Frzb-1/FrzB/Fritz, suppressed TCF-luciferase activity in the hOB cells.

All together, these observations suggest that a Wnt protein(s) prolongs the life of human osteoblasts in vitro and that antagonism of Wnt signaling by SFRP-1/FRP-1/SARP-2 promotes osteoblast cell death. Thus, an inhibitor of SFRP-1/FRP-1/SARP-2 function may increase osteoblast/pre-osteocyte survival and therefore enhance bone formation in vivo.

Using several methods to characterize Wnt expression in the hOB cells (e.g., RT-PCR, GeneChip analysis and cDNA cloning), we have evidence that these cell lines express, to varying degrees, Wnt-2B/13, -3, -4, -5A, and -11. Anyone or all of these Wnts could be involved in prolonging hOB cell life. Wnt-2B/13 is also known as Wnt-x.

Example 13

Use of hOB SFRP in a Screening Method for Anabolic Agents

A new screening paradigm for an anabolic bone agent using SFRP is designed. As outlined in FIG. 17, this screening paradigm uses the hOB cells and SFRP-1/FRP-1/SARP-2 to identify compounds that are capable of preventing or slowing osteoblast cell death. Such compounds act by blocking the ability of SFRP-1/FRP-1/SARP-2 to accelerate hOB cell death. These compounds bind to SFRP-1/FRP-1/SARP-2 and prevent it from binding a Wnt protein, or they may bind to a Wnt and prevent it from binding to SFRP-1/FRP-1/SARP-2. If SFRP-1/FRP-1/SARP-2 has activities that are independent of Wnt-binding (e.g., binding to a cell surface receptor), then these compounds could also act by preventing this Wnt-independent function as well.

Figure 17:
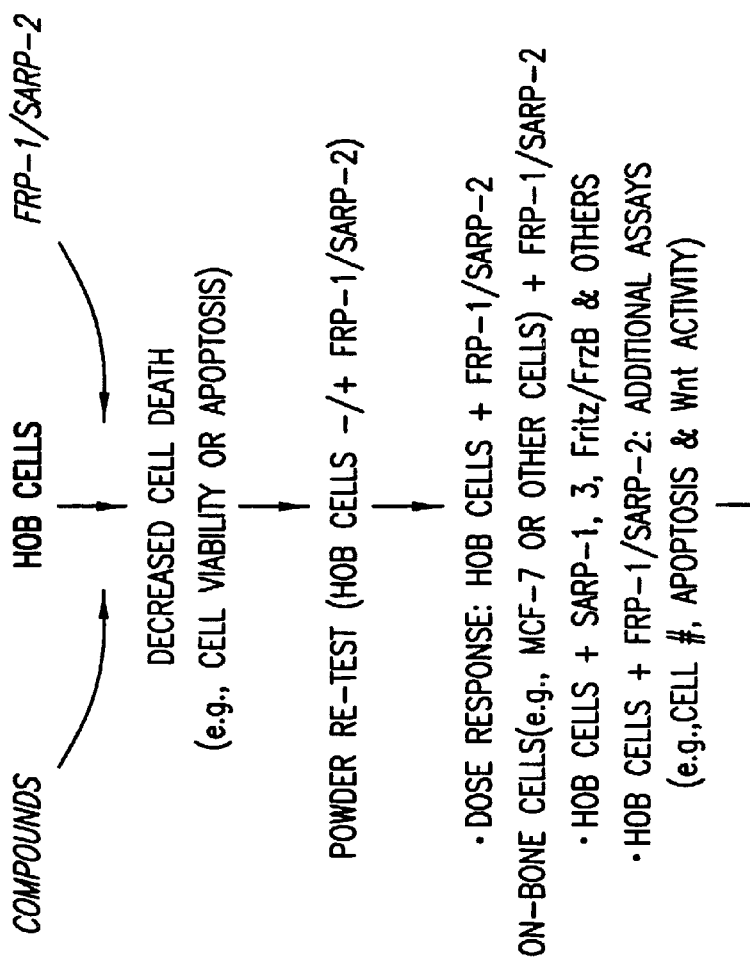
FIG. 17 summarizes a screening paradigm for anabolic bone agents using the hOB cells and hOB SFRP/SFRP-1/FRP-1/SARP-2. This screening paradigm would identify compounds that regulate SFRP-1/FRP-1/SARP-2 function.

For the initial assay of the screening paradigm outlined in FIG. 17, compounds are incubated with an hOB cell line and SFRP-1/FRP-1/SARP-2. This assay could use purified or partially purified SFRP-1/FRP-1/SARP-2 protein, or conditioned-media or cell extracts that contained SFRP-1/FRP-1/SARP-2. The hOB cell line could be one that naturally expressed high basal levels of SFRP-1/FRP-1/SARP-2 (e.g., hOB-01-C1 cells), that transiently or stably overexpressed SFRP-1/FRP-1/SARP-2 (e.g., hOB-01-C1-PS-09 cells), or that stably or naturally expressed SFRP-1/FRP-1/SARP-2 in a conditional manner (e.g., hOB-03-C5 cells treated with $PGE_2$). As a measurement of hOB cell death, assays quantify cell number (e.g., MTT or MTS dye-conversion or CyQuant DNA flourescence) or apoptosis (e.g., DNA fragmentation or annexin V binding) could be used. CyQuant kits were purchased from Molecular Probes (Eugene, Oreg.).

Figure 18:
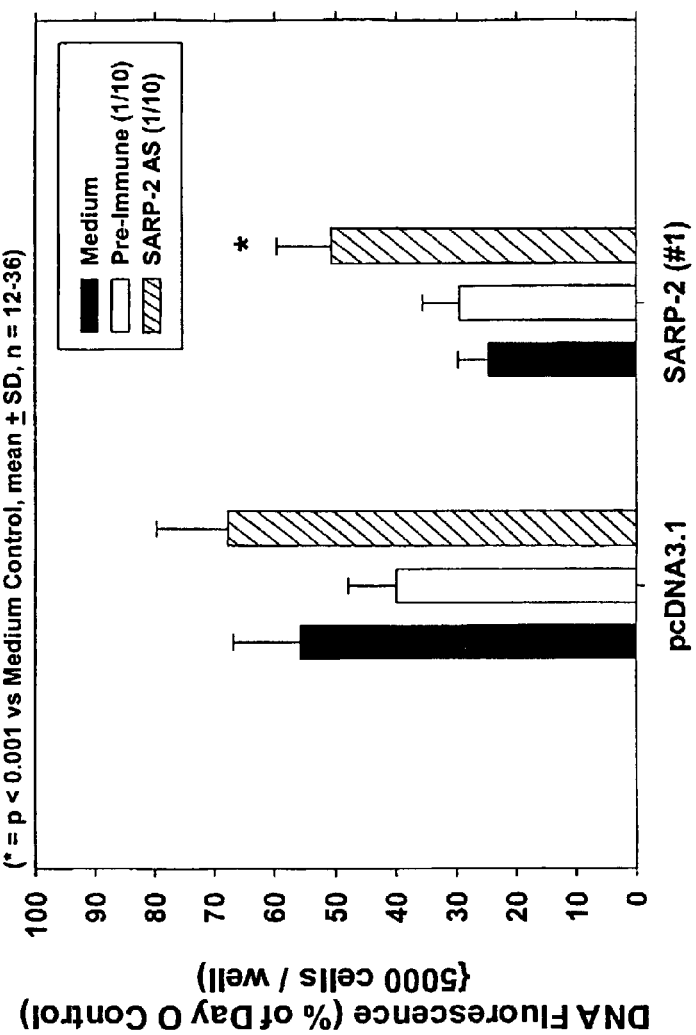
FIG. 18 depicts an example of a high-throughput screening (HTS) assay for compounds that inhibit SFRP-1/FRP-1/SARP-2 function in osteoblastic/osteocytic cells. The results show that the hOB-01-C1-PS-09 cells overexpressing SFRP-1/FRP-1/SARP-2 (SARP-2 #1 cells) die faster than the empty vector expressing cells (pcDNA3.1) using the CyQuant DNA fluorescence assay. Moreover, an antipeptide antiserum to SFRP-1/FRP-1/SARP-2 (SARP-2 AS) blocks the cell death caused by overexpression of this gene.

An example of a high-throughput screening assay (HTS) for SFRP-1/FRP-1/SARP-2 inhibitors is depicted in FIG. 18. For this assay, either empty vector (pcDNA3.1) or SFRP-1/FRP-1/SARP-2 (SARP-2 #1) stable overexpressing hOB-01-C1-PS-09 cells were seeded at 5000 cells per well into 96-well plates using growth medium. After a brief 6 hr incubation at 34° C., the wells were rinsed with PBS and incubated in BSA-medium at 39° C. for 3 days. At the end of the incubation, the wells were rinsed again with PBS and then assayed for DNA content using the CyQuant DNA fluorescence assay (Molecular Probes). When compared to the empty vector cells, the SARP-2 overexpressing cells died faster at 39° C. such that after 3 days, only 20–30% of the cells were still alive. In contrast, 50–60% of the empty vector cells survived the incubation. When the SARP-2 overexpressing cells were treated with an antipeptide antisera (AS) generated to amino acids 217–231 of SFRP-1/FRP-1/SARP-2, 50–60% of the cells were alive after 3 days. This indicates that inhibition of SFRP-1/FRP-1/SARP-2 protein function prevents it from accelerating hOB cell death. As controls, the pre-immune serum had no effect on the SARP-2 overexpressing cells, and neither the pre-immune nor the immune sera affected the empty vector expressing cells.

Compounds that blocked hOB cell death induced by SFRP-1/FRP-1/SARP-2 would then move on to additional in vitro assays. These assays measure the ability of these compounds to block hOB cell death in an SFRP-1/FRP-1/SARP-2-dependent or independent manner, and they would also determine the potency and efficacy of these compounds for these effects. Additional assays are designed to determine the cell selectivity of these compounds for these effects (e.g., by using MCF-7 or other cells), as well as the specificity of these compounds for SFRP-1/FRP-1/SARP-2 versus another member of the SFRP/SARP family (e.g., FrzB/Fritz, SARP-1, or SARP-3). Additional assays could also be used to determine if these compounds regulate down-stream signaling events involved in apoptosis (e.g., caspase activity) or Wnt activity (e.g., β-catenin levels and function via the TCF-luciferase assay). Finally, compounds that exhibited appropriate activities in these in vitro assays would then be used in a variety of animal models for bone formation, osteopenia, or osteoporosis (e.g., ovariectomized rats or mice). A compound that inhibited osteoblast/osteocyte apoptosis would conceivably be an anabolic bone agent by prolonging the lives of these cells and thereby either increasing the amount of bone matrix that is synthesized and mineralized and/or maintaining the integrity of the bone.

It is clear that the invention may be practiced otherwise than as particularly described in the foregoing description and examples. Numerous modifications and variations of the present invention are possible in light of the above teachings and therefore are within the scope of the appended claims.

Example 14

Development and Use of SFRP-1 Knock-Out Mice

As stated in Example 13, a compound that inhibited osteoblast/osteocyte apoptosis would conceivably be an anabolic bone agent by prolonging the lives of these cells and thereby either increasing the amount of bone matrix that is synthesized and mineralized and/or maintaining the integrity of the bone. In order to test this hypothesis and determine if SFRP-1/FRP-1/SARP-2 affects the skeleton, to SFRP-1$^{neg}$ mice were prepared (See Wattler et al. 1999. BioTechniques 26: 1150–1160). Deleting the SFRP-1/FRP-1/SARP-2 gene from mice would be akin to inhibiting its function with a drug, and this process allows us to validate this gene/protein as a potential drug target for osteoporosis.

Figure 19:
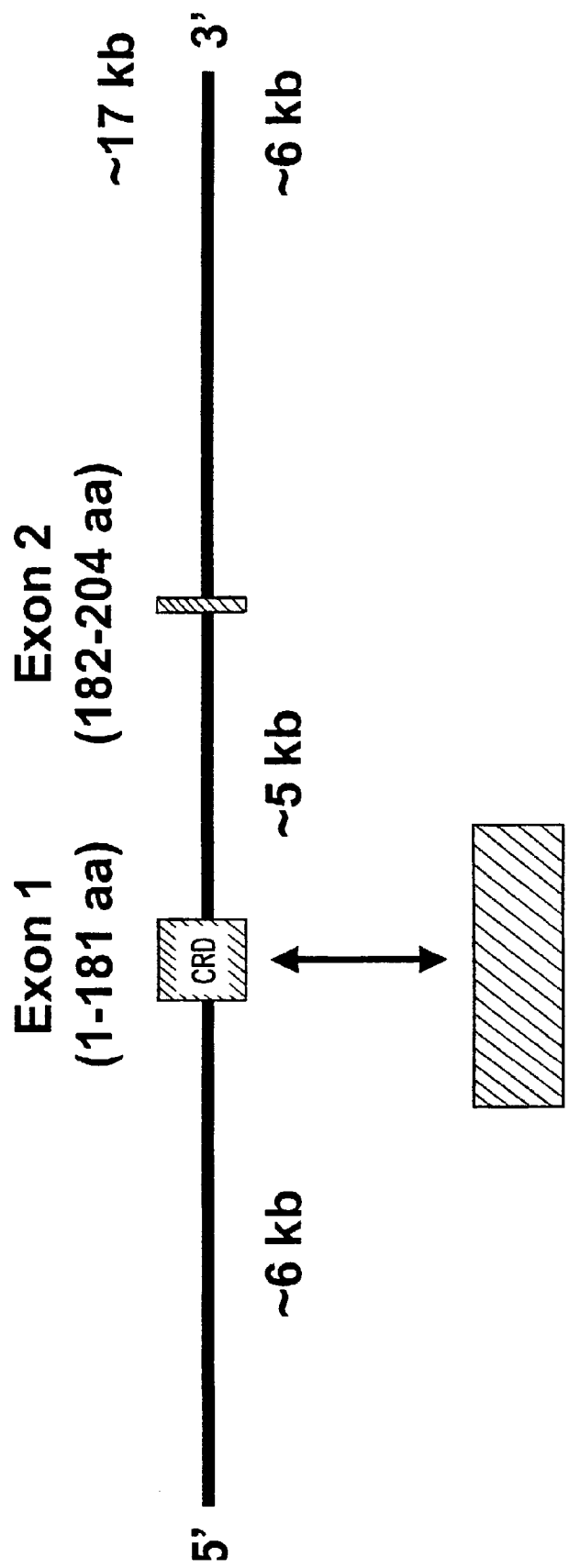
FIG. 19 outlines the strategy that was used to create the SFRP-1/SARP-2 knock-out mice. Exon 1 of the mouse SFRP-1/SARP-2 gene, which encodes for the entire cysteine-rich domain (CRD) was replaced with the expression cassette for β-galactosidase and neomycin resistance.

As summarized in FIG. 19, the SFRP-1 knock-out mice were generated by substituting exon 1 of the mouse SFRP-1 gene with a β-galactosidase reporter gene/neomycin drug resistance gene expression cassette. As shown in FIG. 20, Northern blot analysis of poly A+ RNA isolated from either female of male kidneys (age 16–18 weeks) demonstrated high levels of SFRP-1 mRNA expression (4.4 kb) in the wild-type (WT) control mice, but a complete absence of gene expression in the knock-out (KO) mice.

Figure 21A:
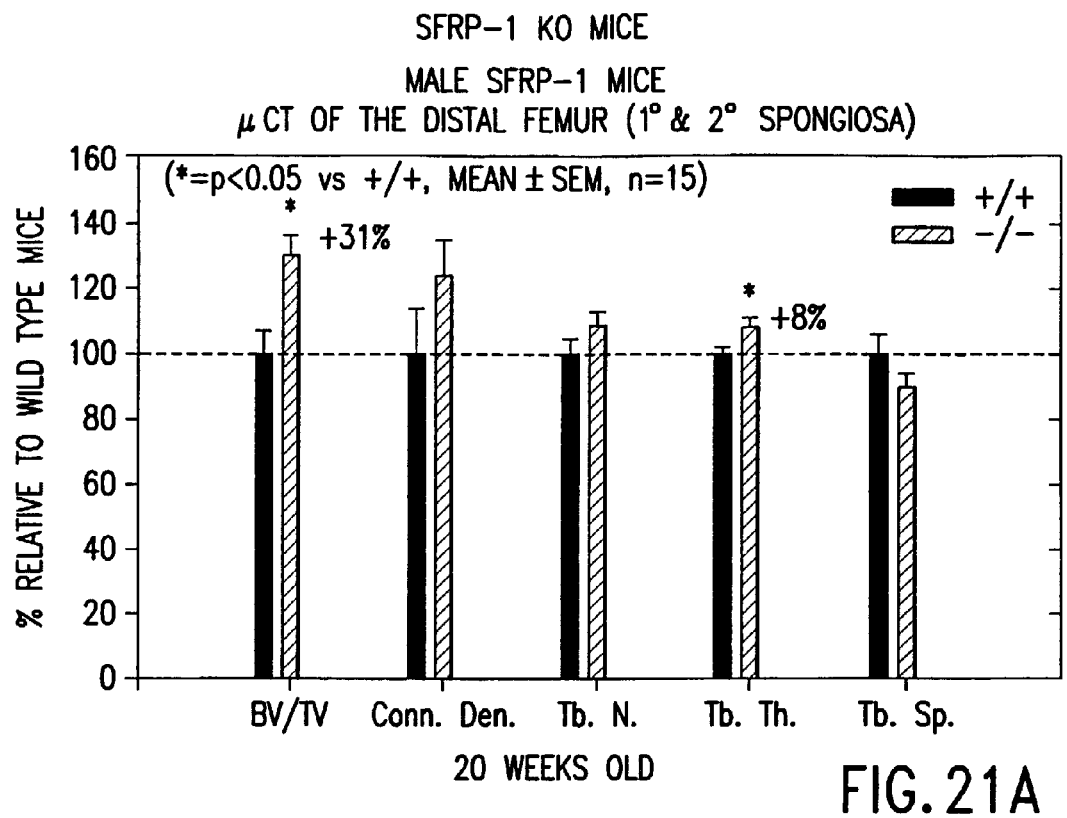
FIG. 21 shows the results of a micro-computerized tomography (micro-CT) analysis of femurs obtained from the male (panel A) and female (panel B) wild-type (+/+) and knock-out (−/−) SFRP-1 mice. When compared to the +/+ control mice, the data demonstrate that the −/− mice exhibit increased parameters of bone formation (i.e., BV/TV, Tb. Th., Conn. Den., Tb. N. & Tb. Sp.) as determined by this method.
Figure 21B:
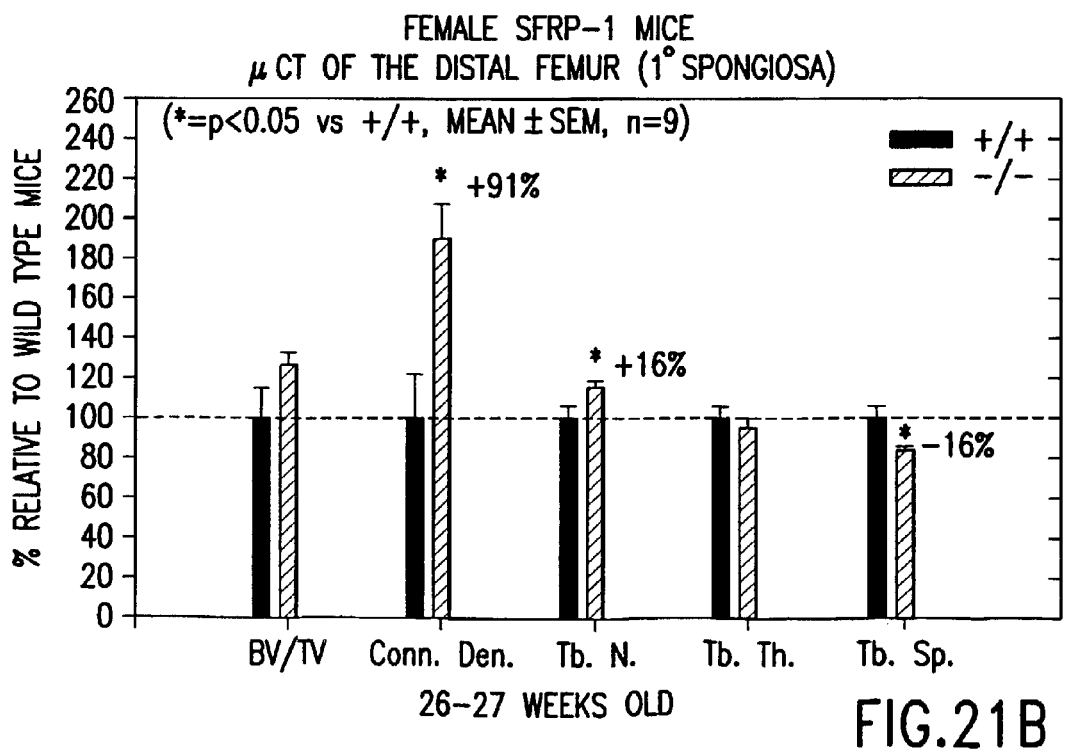

As shown in FIG. 21, micro computerized tomography (micro-CT) was used to characterize the trabecular bone architecture of the distal femurs from male and female wild-type control (+/+) and knock-out (−/−) mice (for a review of this technique, see Genant et al. 1999 Bone 25: 149–152 and Odgaard 1997 Bone 20: 315–328). In the 20 week old males (panel A), the −/− mice had 31% more trabecular bone volume (BV/TV) and an 8% increase in trabecular thickness (Tb. Th.) when compared to the +/+ control mice. In the 26–27 week old females (panel B), the −/− mice had a 91% increase in trabecular connectivity density (Conn. Den.), a 16% increase in trabecular number (Tb. N.) and a 16% decrease in trabecular spacing (Tb. Sp.) when compared to the +/+ control mice. Thus, in support of our hypothesis, these results demonstrate that deletion of the SFRP-1 gene in mice leads to increased parameters of trabecular bone formation (P. J. Meunier 1995 Bone Histomorphometry, in Osteoporosis: Etiology, Diagnosis, and Management, $2^{nd}$ edition, B. L. Riggs & L. J. Melton III, editors, Lippincott-Raven, Philadelphia, pages 299–318).

What is claimed is:

1. A method for identifying test compounds that modulate bone formation in a mammal, which method comprises comparing a bone formation parameter associated with a secreted frizzled related protein (SFRP) in an SFRP (−/−) mouse in the presence of the test compound or compounds with the same bone formation parameter associated with SFRP in an SFRP (−/−) mouse in the absence of the test compound or compounds, wherein an increase or decrease in the bone formation parameter associated with SFRP indicates said compound is a modulator of bone formation in a mammal.

2. The method of claim 1 wherein the bone formation parameter associated with SFRP is selected from the group consisting of trabecular bone volume, trabecular thickness, trabecular connectivity density, trabecular number, and trabecular spacing.

3. The method of claim 1 wherein the bone formation parameter associated with SFRP is cartilage growth.

4. The method of claim 1 wherein the bone formation parameter associated with SFRP is apoptosis of osteoblasts or osteoclasts.

5. The method of claim 4 wherein the apoptosis is measured by CyQuant DNA fluorescence assay.

6. The method of claim 1 wherein the bone formation parameter is a trabecular bone formation parameter.

7. The method of claim 1 wherein the SFRP is mouse SFRP-1.

* * * * *